(12) United States Patent
Kanduluru et al.

(10) Patent No.: US 11,141,494 B2
(45) Date of Patent: Oct. 12, 2021

(54) DEVELOPMENT OF NEUROKININ-1 RECEPTOR-BINDING AGENT DELIVERY CONJUGATES

(71) Applicant: PURDUE RESEARCH FOUNDATION, West Lafayette, IN (US)

(72) Inventors: Ananda Kumar Kanduluru, West Lafayette, IN (US); Philip S. Low, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/501,630

(22) PCT Filed: Aug. 7, 2015

(86) PCT No.: PCT/US2015/044229
§ 371 (c)(1),
(2) Date: Feb. 3, 2017

(87) PCT Pub. No.: WO2013/126797
PCT Pub. Date: Aug. 29, 2013

(65) Prior Publication Data
US 2017/0216465 A1    Aug. 3, 2017

Related U.S. Application Data

(60) Provisional application No. 62/035,427, filed on Aug. 9, 2014.

(51) Int. Cl.
| | | |
|---|---|---|
| *A61K 49/00* | (2006.01) | |
| *C07K 14/705* | (2006.01) | |
| *C09B 23/01* | (2006.01) | |
| *C09B 11/24* | (2006.01) | |
| *A61K 31/404* | (2006.01) | |
| *A61K 51/04* | (2006.01) | |
| *A61K 31/4545* | (2006.01) | |
| *A61K 31/475* | (2006.01) | |
| *A61K 38/05* | (2006.01) | |
| *A61K 51/06* | (2006.01) | |
| *A61K 51/08* | (2006.01) | |

(52) U.S. Cl.
CPC ........ *A61K 49/0052* (2013.01); *A61K 31/404* (2013.01); *A61K 31/4545* (2013.01); *A61K 31/475* (2013.01); *A61K 38/05* (2013.01); *A61K 49/0041* (2013.01); *A61K 51/0455* (2013.01); *A61K 51/0459* (2013.01); *A61K 51/0478* (2013.01); *A61K 51/0482* (2013.01); *A61K 51/06* (2013.01); *A61K 51/08* (2013.01); *C07K 14/70571* (2013.01); *C09B 11/24* (2013.01); *C09B 23/0025* (2013.01); *C09B 23/0066* (2013.01)

(58) Field of Classification Search
None
See application file for complete search history.

(56) References Cited

U.S. PATENT DOCUMENTS

| | | |
|---|---|---|
| 5,561,130 A | 10/1996 | Seward et al. |
| 6,815,423 B1 | 11/2004 | Desjardins et al. |
| 2007/0053837 A1 | 3/2007 | Merlo et al. |

FOREIGN PATENT DOCUMENTS

| | | | |
|---|---|---|---|
| WO | WO-9218536 A2 * | 10/1992 | ............. A61K 51/08 |
| WO | 2013126797 A1 | 8/2013 | |

OTHER PUBLICATIONS

Kobayashi et al. New strategies for fluorescent probe design in medical diagnostic imaging. 2010 Chem. Rev. 110: 2620-2640. (Year: 2010).*
Harrison et al. Piperidine-ether based hNK1 antagonists 2: investigation of the effect of N-substitution. 1995 Bioorg. Med. Chem. Lett. 5: 209-212. (Year: 1995).*
Kularatne et al. Synthesis and biological analysis of prostate-specific membrane antigen-targeted anticancer prodrugs. 2010 J. Med. Chem. 53: 7767-7777. (Year: 2010).*
Turcatti et al. Characterization of non-peptide antagonist and peptide agonist binding sites of the NK1 receptor with fluorescent ligands. 1997 J. Biol. Chem. 272: 21167-21175. (Year: 1997).*
Bennett et al. Analysis of fluorescently labeled substance P analogs: binding, imaging and receptor activation. 2001 BMC Chem. Biol. 1: 1,12 pages. (Year: 2001).*
Payan et al. Substance P recognition by a subset of human T lymphocytes. 1984 J. Clin. Invest. 74: 1532-1539. (Year: 1984).*
Kaiser, et al. "Color Test for Detection of Free Terminal Amino Groups in the Solid-Phase Synthesis of Peptides," Anal Biochem. Apr. 1970; 34(2) pp. 595-598.
Seabrook, et al., "L-733,060, a novel tachykinin NK 1 receptor antagonist; effects in [Ca2+] mobilisation, cardiovascular and dural extravasation assays", European Journal of Pharmacology 317 (1996) pp. 129-135.
International Preliminary Report on Patentability (Chapter 1 of the Patent Cooperation Treaty) in International Application No. PCT/US2015/044229 dated Feb. 23, 2017.

* cited by examiner

*Primary Examiner* — Jennifer Lamberski
(74) *Attorney, Agent, or Firm* — Schwegman Lundberg & Woessner, P.A.

(57) ABSTRACT

Neurokinin-1 (NK-1) receptor-binding agent delivery conjugates, compositions comprising NK-1 receptor-binding agent delivery conjugates, and methods for making and administering NK-1 receptor-binding agent delivery conjugates are provided. A conjugate may include an NK-1 receptor-binding moiety, a linker group containing at least one linker selected from the group of a releasable linker and a spacer linker, and an active agent linked to the linker group. The active agent may be selected from the group of fluorophore-containing compounds, radionuclide-containing compounds, and therapeutic agents for treatment of tumor cells characterized by over-expression of the NK-1 receptor.

5 Claims, 23 Drawing Sheets

DEVELOPMENT OF NEUROKININ-1 RECEPTOR-BINDING AGENT DELIVERY CONJUGATES

RELATED APPLICATIONS

This is a U.S. national stage application under 35 U.S.C. § 371 of PCT/US2015/04429, filed internationally on Aug. 7, 2015, which claims the benefit of priority to U.S. Provisional Application No. 62/035,427, filed Aug. 9, 2014, both of which are hereby incorporated by reference in their entireties.

BACKGROUND

The mammalian immune system provides mechanisms for the recognition and elimination of tumor cells invading foreign pathogens. While the immune system normally provides a strong line of defense, tumor cells or pathogens may nonetheless evade a host immune response and proliferate or persist with concomitant host pathogenicity. Chemotherapeutic agents and radiation therapies have been developed to eliminate, for example, replicating neoplasms. However, many of the currently available chemotherapeutic agents and radiation therapy regimens have adverse side effects by likewise affecting normal host cells, such as cells of the hematopoietic system. The adverse side effects of these anticancer drugs highlight the need for the development of new therapies selective for pathogenic cell populations and with reduced host toxicity. Moreover, the target selectiveness can be implemented to improve other therapeutic and diagnostic techniques that are tailored to a pathogenic cell population.

Researchers have developed therapeutic protocols for destroying pathogenic cells by targeting cytotoxic compounds to such cells. Many of these protocols utilize toxins or chemotherapeutic agents conjugated to antibodies that bind to antigens that are unique to, or over-expressed by, the pathogenic cells in an attempt to minimize delivery of the toxin to normal cells.

The neurokinin-1 (NK-1) receptor (also known as the tachykinin receptor 1 or SP receptor) is a G protein-coupled receptor that is the product of the TACR1 gene. The NK-1 receptor is 407 amino acid residues, and, along with other tachykinin receptors, is made of seven hydrophobic transmembrane domains with three extracellular and three intracellular loops, an amino-terminus, and a cytoplasmic carboxy-terminus. The loops have functional sites, including two cysteines amino acids for a disulfide bridge, Asp-Arg-Tyr that is responsible for association with arrestin, and Lys/Arg-Lys/Arg-X—X-Lys/Arg, which interacts with G-proteins. While the NK-1 receptor has some affinity for all tachykinins, its endogenous ligand is the peptide Substance P (SP).

Upon binding to the NK-1 receptor, SP has been shown to induce changes such as tumor cell proliferation, angiogenesis, and migration of the tumor cells for metastasis. In contrast, NK-1 receptor antagonists exert antiproliferative effects on NK-1-receptor expressing cells by inducing apoptosis. Moreover, it is known that NK-1 receptors are over-expressed in some tumors, and that tumor cells express several isoforms of the NK-1 receptor. For example, NK-1 receptor over-expression has been reported in certain cancers of the larynx, stomach, colon, pancreas, and breast as well as glioblastomas, gliomas, astrocytomas, melanomas, retinoblastomas, and neuroblastomas.

All of these data suggest that NK-1 receptor expression may play an important role in the development of cancer, that SP may be a universal mitogen in NK-1 receptor-expressing tumor cells, and/or that expression of the NK-1 receptor may be utilized to diagnose or identify specific tumors. Further, the data suggest that NK-1 receptor antagonists could offer a promising therapeutic strategy for the treatment of human cancer, since they act as broad-spectrum antitumor agents. In sum, the NK-1 receptor may be a new and promising target in the diagnosis and/or treatment of human cancer.

SUMMARY

The various embodiments provide compositions and methods for making and administering a neurokinin-1 (NK-1) receptor-binding agent delivery conjugate that includes an NK-1 receptor-binding moiety, a linker group that includes one or more linker selected form the group of a releasable linker and a spacer linker, and an active agent linked to the linker group.

In some embodiments, the linker group includes at least one spacer linker, and the active agent is selected from the group consisting of a fluorophore-containing compound and a radionuclide-containing compound. In some embodiments, the linker group includes at least one releasable linker, and the active agent is a therapeutic agent. In some embodiments, the active agent is a radionuclide-containing compound including one of technetium-99m and copper-64, and a chelating portion that forms a complex with the radionuclide.

In some embodiments, the active agent is a therapeutic agent for treatment of tumor cells characterized by over-expression of the NK-1 receptor, in which the therapeutic agent is selected from the group of tubulysin B hydrazide (TubH) and disulfide-activated desacetyl vinblastine hydrazide (DAVBH).

BRIEF DESCRIPTION OF THE DRAWINGS

The accompanying drawings, which are incorporated herein and constitute part of this specification, illustrate example aspects of the invention, and together with the general description given above and the detailed description given below, serve to explain the features of the invention.

DETAILED DESCRIPTION

Figure 1A:
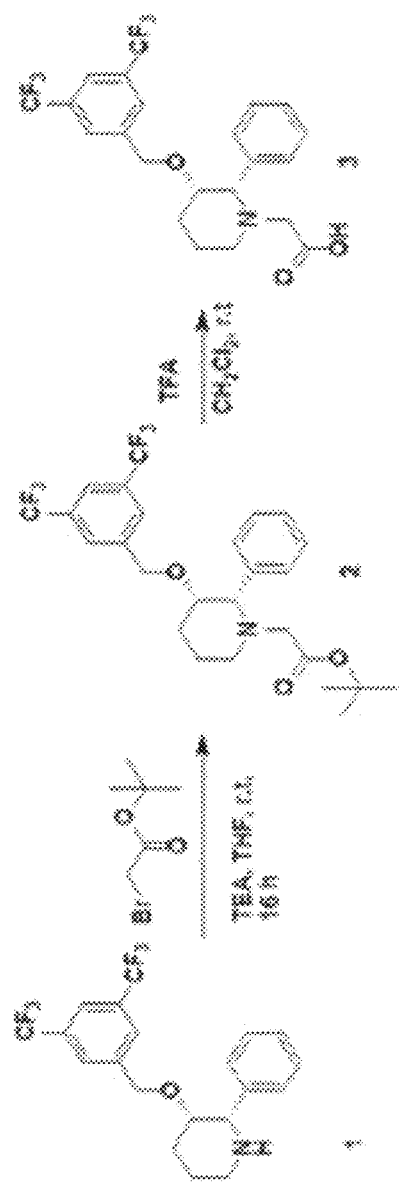
FIG. 1A is a schematic reaction equation illustrating the formation of an NK-1 receptor-binding moiety.

The present invention may be understood more readily by reference to the following detailed description taken in connection with the accompanying figures and examples, which form a part of this disclosure. It is to be understood that the various embodiments are not limited to the specific devices, methods, applications, conditions or parameters described and/or shown herein, and that the terminology used herein is for the purpose of describing particular embodiments by way of example only and is not intended to be limiting.

It is to be appreciated that certain features that are, for clarity, described herein in the context of separate embodiments, may also be provided in combination in a single embodiment. Conversely, various features that are, for brevity, described in the context of a single embodiment, may also be provided separately or in any sub-combination. Further, reference to values stated in ranges include each and every value within that range.

As used in this specification and the appended claims, the singular forms "a," "an," and "the" include plural referents unless the content clearly dictates otherwise.

The term "alkyl" as used herein refers to a monovalent linear chain of carbon atoms that may be optionally branched, such as methyl, ethyl, propyl, 3-methylpentyl, and the like.

The term "cycloalkyl" as used herein refers to a monovalent chain of carbon atoms, a portion of which forms a ring, such as cyclopropyl, cyclohexyl, 3-ethylcyclopentyl, and the like.

The term "alkylene" as used herein refers to a bivalent linear chain of carbon atoms that may be optionally branched, such as methylene, ethylene, propylene, 3-methylpentylene, and the like.

The term "cycloalkylene" as used herein refers to a bivalent chain of carbon atoms, a portion of which forms a ring, such as cycloprop-1,1-diyl, cycloprop-1,2-diyl, cyclohex-1,4-diyl, 3-ethylcyclopent-1,2-diyl, 1-methylenecyclohex-4-yl, and the like.

The term "heterocycle" as used herein refers to a monovalent chain of carbon and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like.

The term "alkoxy" as used herein refers to alkyl as defined herein combined with a terminal oxygen, such as methoxy, ethoxy, propoxy, 3-methylpentoxy, and the like.

The term "halo" or "halogen" refers to fluoro, chloro, bromo, and iodo.

The term "aryl" as used herein refers to an aromatic mono or polycyclic ring of carbon atoms, such as phenyl, naphthyl, and the like.

The term "heteroaryl" as used herein refers to an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term "substituted aryl" or "substituted heteroaryl" as used herein refers to aryl or heteroaryl substituted with one or more substituents selected, such as halo, hydroxy, amino, alkyl or dialkylamino, alkoxy, alkylsulfonyl, cyano, nitro, and the like.

The term "iminoalkylidenyl" as used herein refers to a divalent radical containing alkylene as defined herein and a nitrogen atom, where the terminal carbon of the alkylene is double-bonded to the nitrogen atom, such as the formulae —(CH)=N—, —(CH$_2$)$_2$(CH)=N—, —CH$_2$C(Me)=N—, and the like.

The term "amino acid" as used herein refers generally to aminoalkylcarboxylate, where the alkyl radical is optionally substituted with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like.

The term "arylalkyl" refers to aryl as defined herein substituted with an alkylene group, as defined herein, such as benzyl, phenethyl, α-methylbenzyl, and the like.

It should be understood that the above-described terms can be combined to generate chemically-relevant groups, such as "alkoxyalkyl" referring to methyloxymethyl, ethyloxyethyl, and the like, and "haloalkoxyalkyl" referring to trifluoromethyloxyethyl, 1,2-difluoro-2-chloroeth-1-yloxypropyl, and the like.

The term "amino acid derivative" as used herein refers generally to aminoalkylcarboxylate, where the amino radical or the carboxylate radical are each optionally substituted with alkyl, carboxylalkyl, alkylamino, and the like, or optionally protected; and the intervening divalent alkyl fragment is optionally substituted with alkyl, hydroxy alkyl, sulfhydrylalkyl, aminoalkyl, carboxyalkyl, and the like, including groups corresponding to the side chains found in naturally occurring amino acids, such as are found in serine, cysteine, methionine, aspartic acid, glutamic acid, and the like.

The term "peptide" as used herein refers generally to a series of amino acids and amino acid analogs and derivatives covalently linked one to the other by amide bonds.

The term "releasable linker" as used herein refers to a linker that includes at least one bond that can be broken under physiological conditions (e.g., a pH-labile, acid-labile, redox-labile, or enzyme-labile bond). It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH.

The term "spacer linker" as used herein refers to an organic moiety that separates the active agent or releasable linker from the NK-1 receptor-binding moiety.

In cancer treatment, the use of conventional chemotherapeutics may be limited due to their indiscriminate accumulation in both cancer and healthy cells, thereby resulting in dose-limiting toxicities in untargeted healthy tissues. One mechanism to overcome such general accumulation may be selective ligand-targeted delivery of cytotoxic agents to malignant tissues. In particular, various embodiments provide for uses of NK-1 receptor-targeted ligands to provide therapeutic and imaging agents for use in diagnosis and treatment of cancer.

The various embodiments provide NK-1 receptor-binding agent delivery conjugates that enable improved mechanisms for targeted delivery of active agents to cells expressing NK-1 receptors. In particular, the various embodiment compounds may include an NK-1 receptor-binding moiety (NK), at least one linker group (L), and at least one active agent (A) (e.g., a drug, a fluorescent dye, a radioimaging agent, and/or a combination thereof). In the various embodiments, the NK-1 receptor-binding moiety and the active agent may be bound to the linker group.

The linker groups in the various embodiments may include one or more spacer linkers and releasable linkers, and combinations thereof, in any order. The various active agents and linker groups discussed below are provided as non-limiting examples, for which alternatives are described in International Published Patent Application No. WO2013/126797, the disclosure which is incorporated herein by reference in its entirety.

Active Agents

The active agents D of the conjugates of the present invention may, in various embodiments, be therapeutic agents and/or imaging agents. The only limitation on suitable therapeutic agents and imaging agents is the requirement that they have a position on the molecule to which can be conjugated the linker L, or that they can be derivatized to possess such a position without losing the activity of the active moiety or compromising the ability of the NK-1 receptor-binding moiety to bind to its receptor with high affinity.

The therapeutic agents described herein function through any of a large number of mechanisms of action. Generally, therapeutic agents disrupt cellular mechanisms that are important for cell survival and/or cell proliferation and/or cause apoptosis. By way of example only, the therapeutic agents can be any compound known in the art which is cytotoxic, enhances tumor permeability, inhibits tumor cell proliferation, promotes apoptosis, decreases anti-apoptotic activity in target cells, is used to treat diseases caused by infectious agents, enhances an endogenous immune response directed to the pathogenic cells, or is useful for treating a disease state caused by any type of pathogenic cell.

Therapeutic agents suitable for use in accordance with this invention include, without limitation, adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, taxanes, such as tamoxiphen, taxol, paclitaxel, paclitaxel derivatives, Taxotere®, and the like, maytansines and analogs and derivatives thereof, cyclophosphamide, daunomycin, doxorubicin, rhizoxin, T2 toxin, plant alkaloids, prednisone, hydroxyurea, teniposide, mitomycins, discodermolides, microtubule inhibitors, epothilones, tubulysin (e.g., tubulysin B hydrazide), cyclopropyl benz[e]indolone, seca-cyclopropyl benz[e]indolone, O—Ac-seca-cyclopropyl benz[e]indolone, bleomycin and any other antibiotic, nitrogen mustards, nitrosureas, vincristine, vinblastine, and analogs and derivative thereof such as desacetyl vinblastine monohydrazide, colchicine, colchicine derivatives, allocolchicine, thiocolchicine, trityl cysteine, Halicondrin B, dolastatins such as dolastatin 10, amanitins such as a-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include penicillins, dinitrophenol, fluorescein, CpG oligonucleotides, staurosporine and othe kinase inhibitors, Sutent, resiquimod and other Toll-like receptor agonists, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other art-recognized antimicrobial compound.

Specific sub-groups of therapeutic agents include, but are not limited to, radio-therapeutic agents, immunotherapeutic agents, photodynamic therapy agents and chemo therapeutic agents. The skilled artisan will understand that there is a wide variety of radio-therapeutics that will be suitable for use in the conjugates of the present invention. Suitable examples include, but are not limited to, $^{90}$Y, $^{131}$I, $^{177}$Lu, $^{67}$Cu, $^{111}$In, $^{186}$Re, $^{211}$At, and $^{223}$Ra.

The skilled artisan will also understand that there is a wide variety of chemotherapeutics that will be suitable for use in the conjugates of the present invention. Suitable examples include, but are not limited to, tubulysin B hydrazide and desacetyl vinblastine monohydrazide, calicheamycin, auristatin, maytansinoids, and any other cytotoxic agent with $IC_{50}$ value below 10 nM.

It should also be appreciated that the ligand can be used to target a nanomedicines or nanoparticle, including but not limited to a liposome, a lipoplex, a polyplex, a dendrimer, a polymer, a nanoparticle, or a virus. It should further be recognized that the aforementioned particles might serve as carriers for DNA, RNA, siRNA, peptides, proteins, and other biologies.

Imaging agents suitable for use in the conjugates of the invention include, but are not limited to, radio-imaging agents, optical imaging agents, PET imaging agents, MRI contrast agents, CT contrast agents, and FRET imaging agents, and other agents that may be used to detect or visualize a tumor, cancer or transformed cell, whether in vitro, in vivo and ex vivo.

Applications for conjugates comprising radio-imaging agents include, but are not limited to, diagnosis of disease and or locating metastatic disease, detecting disease recurrence following surgery, monitoring response to therapy, development of a radio-therapeutic conjugate and selecting patients for subsequent CCK2R targeted therapy. Radio-imaging agents include radioactive isotopes, such as a radioactive isotope of a metal, coordinated to a chelating group. Illustrative radioactive metal isotopes include technetium, rhenium, gallium, gadolinium, indium, copper, and the like, including isotopes $^{111}$In, $^{99m}$Tc, $^{64}$Cu, $^{67}$Cu, $^{67}$Ga, $^{68}$Ga, and the like, or they may include radionuclides that are effective in radiotherapy.

Illustratively, the following chelating groups are described that can be used with the radio-imaging agents:

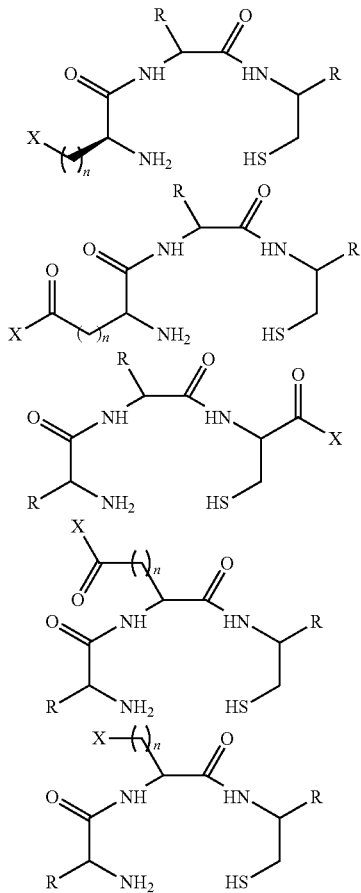

wherein R is independently selected in each instance from, for example, H, alkyl, heteroalkyl, cycloalkyl, heterocyclyl, alkenyl, alkynyl, aryl, heteroaryl, arylalkyl, heteroarylalkyl, and the like, each of which is optionally substituted, wherein one R includes a heteroatom, such as nitro, oxygen, or sulfur, and is the point of attachment of linker L; X is oxygen, nitrogen, or sulfur, and X is attached to linker L; and n is an integer from 1 to about 5.

Additional illustrative chelating groups are tripeptide or tetrapeptides, including but not limited to tripeptides having the formula:

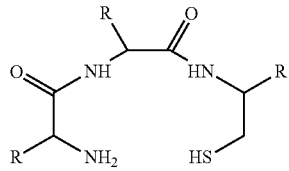

wherein R is independently selected in each instance from H, alkyl, heteroalkyl, cycloalkyl, heterocyclyl, alkenyl, alkynyl, aryl, heteroaryl, arylalkyl, heteroarylalkyl, and the like, each of which is optionally substituted. It is to be understood that one R includes a heteroatom, such as nitro, oxygen, or sulfur, and is the point of attachment of linker L.

Applications for conjugates comprising optical imaging agents include locating and resecting large tumor masses, delineation of normal and malignant tissue, intraoperative detection of sentinel lymph nodes, and fluorescent probe for minimally invasive laparoscopic procedures as an alternative to second look surgery. The skilled artisan will also understand that there is a wide variety of optical imaging agents that will be suitable for use in the conjugates of the present invention. The only limitations on suitable optical imaging agents is the requirement that they have a position on the molecule to which can be conjugated the linker L, or that they can be derivatized to possess such a position. Examples include, but are not limited to, Oregon Green fluorescent agents, including but not limited to Oregon Green 488, Oregon Green 514, and the like, AlexaFluor fluorescent agents, including but not limited to AlexaFluor 488, AlexaFluor 647, and the like, fluorescein, and related analogs, BODIPY fluorescent agents, including but not limited to BODIPY Fl, BODIPY 505, S0456, and the like, rhodamine fluorescent agents, including but not limited to tetramethylrhodamine, and the like, near infra-red fluorescent agents, including but not limited to DyLight 680, DyLight 800, 800CW, LS288, S0456, indocyanine green and the like, Texas Red, phycoerythrin, and others. Illustrative optical imaging agents are shown in the following general structure:

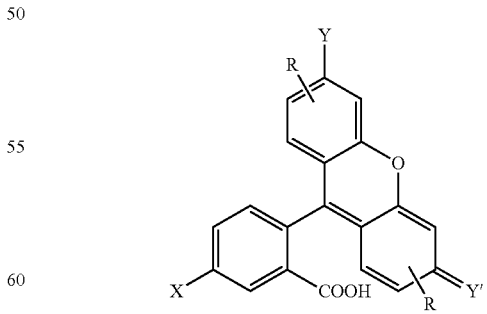

where X is oxygen, nitrogen, or sulfur, and where X is attached to linker L; Y is ORa, NRa$_2$, or NRa$_{3+}$; and Y' is O, NRa, or NRa$_{2+}$; where each R is independently selected in each instance from H, fluoro, sulfonic acid, sulfonate, and salts thereof, and the like; and Ra is hydrogen or alkyl.

According to another aspect, illustrative optical imaging agents are shown in the following general structure:

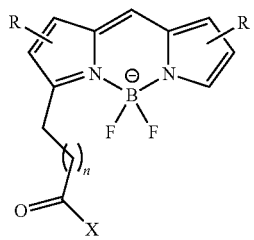

where X is oxygen, nitrogen, or sulfur, and where X is attached to linker L; and each R is independently selected in each instance from H, alkyl, heteroalkyl, and the like; and n is an integer from 0 to about 4.

The skilled artisan will also understand that there is a wide variety of PET imaging agents and FRET imaging agents that will be suitable for use in the conjugates of the present invention. The only limitations on suitable PET and FRET imaging agents is the requirement that they have a position on the molecule to which can be conjugated the linker L, or that they can be derivatized to possess such a position. Examples of PET imaging agents include, but are not limited to, $^{18}$F, $^{11}$C, $^{64}$Cu, $^{65}$Cu, and the like. Examples of FRET imaging agents include, but are not limited to, $^{64}$Eu, $^{65}$Eu, and the like. It appreciated that in the case of $^{18}$F and $^{11}$C, the imaging isotope may be present on any part of the linker, or alternatively may be present on a structure attached to the linker. For example in the case of $^{18}$F, fluoroaryl groups, such as fluorophenyl, difluorophenyl, fluoronitrophenyl, and the like are described. For example in the case of $^{11}$C, alkyl and alkyl aryl are described. Exemplary optical imaging agents include, but are not limited to, fluorescein (FITC), rhodamine, LS288, S0456, IR800CW, or another near infrared dye.

Linkers

Exemplary linkers may include, but are not limited to, hydrophilic linkers comprised of charged or polar amino acids, sugars or sugar-containing oligomers, and hydrophilic polymers such as polyethylene glycol.

In a first embodiment, the linker L is L1, L2 or L3, where L1 is HN-Glu-Arg-Asp-CO, L2 is HN-Glu-PS-Glu-PS—CO, and L3 is HN-Octanoyl-Glu-PS-Glu-PS—CO, in which PS has the following formula:

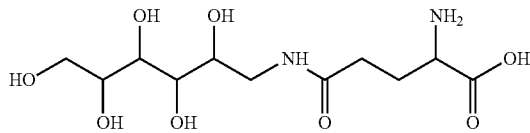 [SMILES: NC(CCC(=O)NCC(O)C(O)C(O)C(O)CO)C(=O)O]

The linkers used in the production of the embodiment compounds may also comprise one or more spacer linkers and/or one or more releasable linkers, and combinations thereof, in any order. It is appreciated that spacer linkers may be included when predetermined lengths are selected for separating the NK-1 receptor-binding moiety from the active agent. It is also appreciated that in certain configurations, releasable linkers may be included.

In an example, the linker group may be a releasable linker that includes a cleavable bond connecting two adjacent atoms. Following breakage of the cleavable bond, the releasable linker may be broken into two or more fragments. In another example the releasable linker may contain a cleavable bond that connects one end of the releasable linker to other linkers, to the active agent, or to the NK-1 receptor-binding moiety. Following breakage of the cleavable bond, the releasable linker may be separated from the other moiety. Examples of a releasable linker may include, but are not limited to, a disulfide group and a carbamate group.

In a particular application, expression of NK-1 receptors has been reported in a number of lethal cancers of the brain (glioblastoma, glioma and astrocytoma), skin (melanoma), pancreas, retina (retinoblastoma), nerve (neuroblastoma), larynx, stomach, colon and breast. Therefore, in various embodiments, the NK-1 receptor-binding agent delivery conjugates may be used to treat and/or diagnose disease states and/or tissues characterized by the presence of a pathogenic cell population having accessible NK-1 receptors that are uniquely expressed, overexpressed, or preferentially expressed by the pathogenic cells (i.e., not present or present at lower concentrations on non-pathogenic cells). Selective elimination, tracing, or imaging of pathogenic cells may therefore be mediated by the binding of the NK-1 receptor-binding moiety to the NK-1 receptor.

Specifically, over-expression of NK-1 receptors has been reported in lethal cancers of the brain (glioblastoma, glioma and astrocytoma), skin (melanoma), pancreas, retina (retinoblastoma), nerve (neuroblastoma), larynx, stomach, colon and breast, the various embodiments may be used to develop an NK1R-targeted NIR dye for use in cancer. Specifically, because NK-1 receptor-binding agent delivery conjugates are typically unable to cross the blood brain barrier, they may fail to reach the vast majority of NK-1 receptors present in normal brain tissues. Instead, an NK-1 receptor-binding agent delivery conjugate may selectively accumulate in NK1R-expressing tumor xenografts with very high affinity, allowing targeted delivery of the active agents to NK-1 receptor expressing tumor cells.

In the various embodiments, the NK-1 receptor-binding moiety may be any of a number of ligands, such as a small molecule ligand customized to be highly selective for NK-1 receptors. For example, the small molecule ligand may have a dissociation constant (KD) of around 13 nM for the NK-1 receptor.

An example NK-1 receptor-binding ligand ("NK1RL") may be synthesized from a high affinity NK-1 receptor antagonist (2S,3S)-3-{[3,5-bis(trifluoromethyl)benzyl]oxy}-2-phenylpiperidine ("L733060") and acetic acid (AcOH), and has the formula:

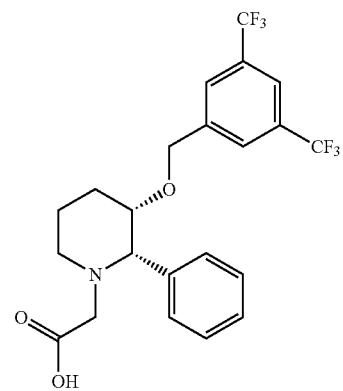 [SMILES: O=C(O)CN1CCC[C@H](OCc2cc(C(F)(F)F)cc(C(F)(F)F)c2)[C@@H]1c1ccccc1]

In a first set of embodiments, the active agent of the NK-1 receptor-binding agent delivery conjugate may be a drug for therapy in order to treat NK-1 receptor positive tumor bearing tissue, as may be shown in mouse xenograft models expressing NK-1 receptors. Example drugs may include, but are not limited to, tubulysin B hydrazide (TubH)) and disulfide-activated desacetyl vinblastine hydrazide (DAVBH). In such drug conjugates, an example linker group may include PEG2 coupled to a peptide that contains a chelating portion of etarfolatide. In particular, the linker group may be PEG2-Arg-Asp-Lys-2,3 diaminopropionic acid (DAP)-Asp-Cys (referred to herein as "EC20 peptide" linker), which has a formula of:

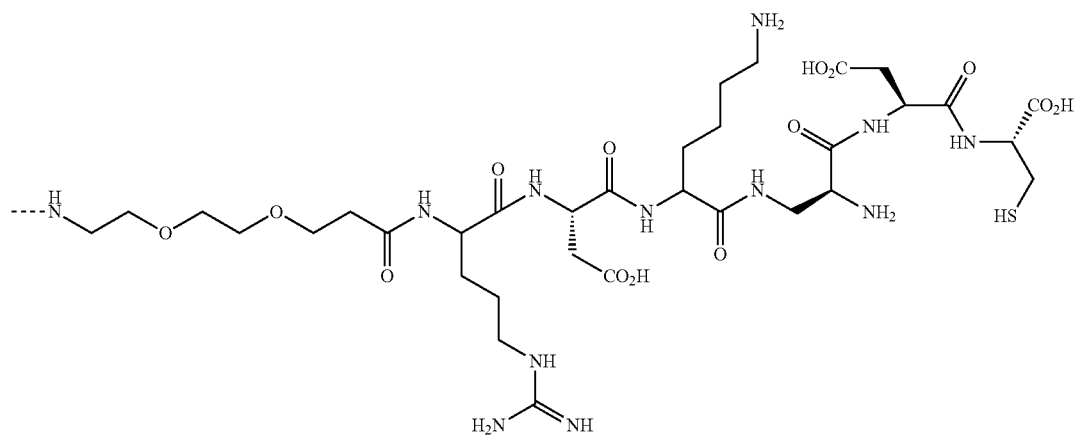

In another example drug conjugate, the linker group may be synthesized from a cysteine-based resin, similar to the EC20 peptide linker, but may contain PEG2 that is coupled to a shorter peptide compared to the EC20 peptide linker. In particular, the linker group may be PEG2-Arg-Asp-Cys (referred to herein as "Cys peptide" linker), which has a formula of:

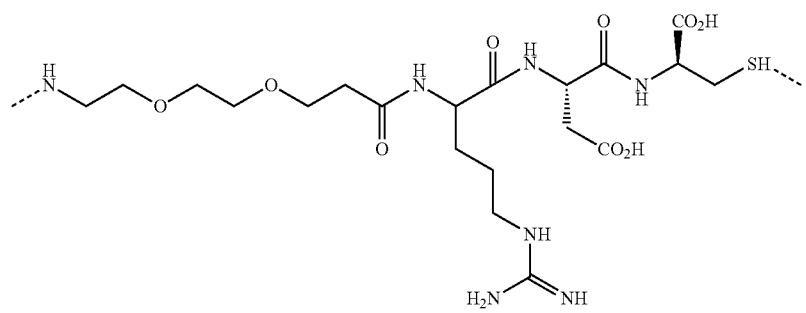

In another example drug conjugate, the linker group may be synthesized from a cysteine-based resin, similar to the EC20 peptide linker and Cys peptide linker, but may contain any of a variety of PEG structures coupled to a shorter peptide that contains the chelating portion of etarfolide. In particular, the linker group may be $PEG_n$-2,3 diaminopropionic acid (DAP)-Asp-Cys (referred to herein as "short EC20" linker). For example, a short EC20 linker may include PEG2 (PEG2-based short EC20 linker) and have a formula of:

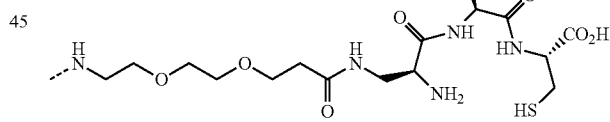

Another example PEG short EC20 linker may include PEG12 (PEG12-based short EC20 linker) and have a formula of:

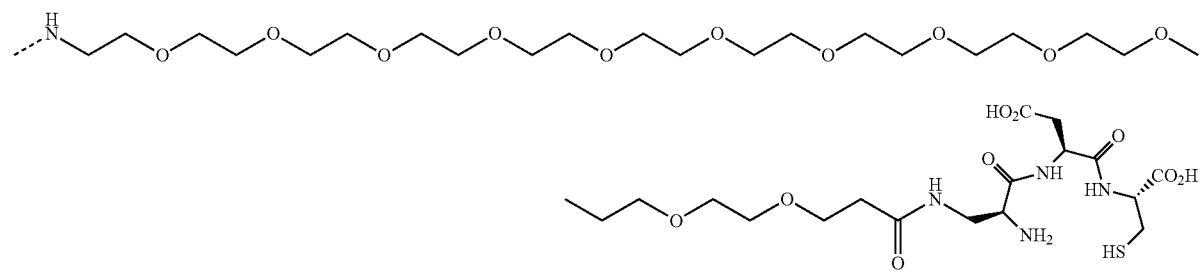

Another example PEG short EC20 linker may include PEG36 (PEG36-based short EC20 linker) and have a formula of:

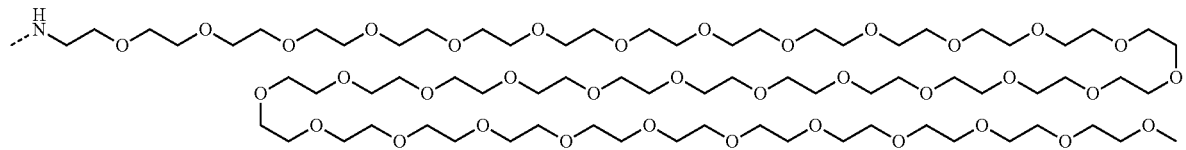

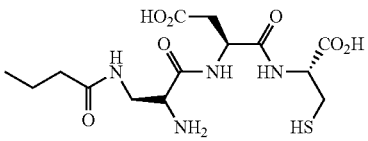

In another example, the linker group may contain one or more peptide sugar (PS) chains in addition to the short EC20 linker. For example, the linker group may include two PS chains coupled to a PEG2-based short EC20 linker. Such linker group (PS2-PEG2-based short EC20 linker) may have a formula of:

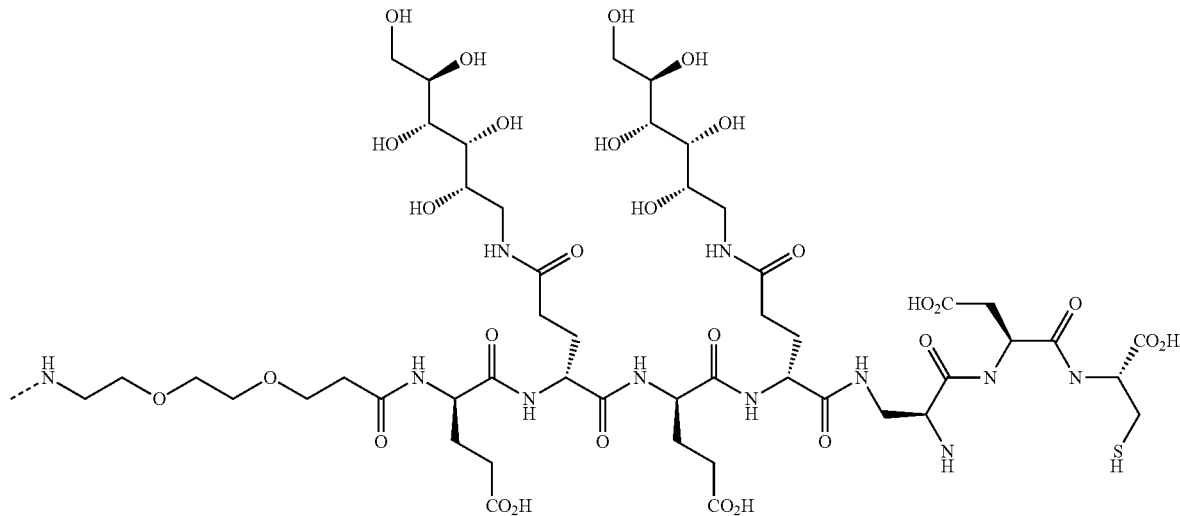

In another example, the linker group may include a short EC20 linker that is free of PEG (i.e., PEG0-based short EC20 linker), which is coupled to one or more PS chain. Such linker group (PS2-PEG0-based short EC20 linker) may have a formula of:

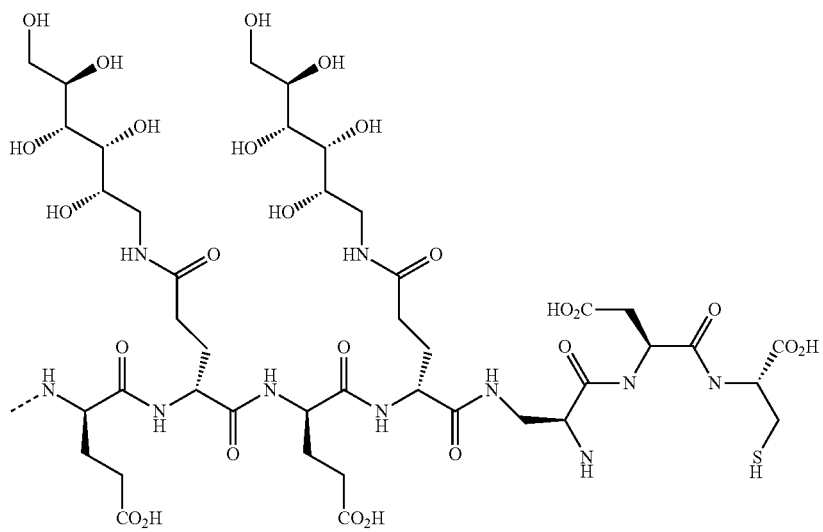

In another set of embodiments, the active agent of the NK-1 receptor-binding agent delivery conjugate may be a radioimaging conjugate. For example, the active agent (i.e., radioimaging agent) may be a radiotagged element for use in single-photon emission computed tomography (SPECT) and/or positron emission tomography (PET) imaging of tumor tissue, and may be shown in mouse xenograft models expressing NK-1 receptors.

In some embodiment radioimaging conjugates, the active agent may be a radiopharmaceutical containing a chelator linked to a radiotag, such as technetium-99m ($^{99m}Tc$). $^{99m}Tc$ is a metastable nuclear isomer of technetium-99 ($^{99}Tc$), and is the most commonly used medical radioisotope. When used as a radioactive tracer, $^{99m}Tc$ can be detected in the body by medical equipment (gamma cameras). $^{99m}Tc$ emits readily detectable 140 keV gamma rays (these 8.8 pm photons are about the same wavelength as emitted by conventional X-ray diagnostic equipment) and its half-life for gamma emission is 6.0058 hours (meaning 93.7% of it decays to $^{99}Tc$ in 24 hours). The "short" physical half-life of the $^{99m}Tc$ isotope and its biological half-life of 1 day (in terms of human activity and metabolism) allow for scanning procedures that collect data rapidly but keep total patient radiation exposure low. The same characteristics make the isotope suitable only for diagnostic but never therapeutic use.

In other radioimaging conjugates, the active agent may include a radionuclide suitable for use as a tracer in PET imaging. For example, Copper-64 ($^{64}Cu$) is a positron emitter that may be well suited for in vitro and in vivo characterization of peptide probes. Radioimaging conjugates in which $^{64}Cu$ labeling is used may also be applied to other copper isotopes and transition metal isotopes for the purposes of radionuclide imaging. In some embodiments, a radioimaging agent may be a $^{64}Cu$ radio-labeled chelator of 1,4,7-triazacyclononane-1,4,7-triacetic acid (NOTA). An example radioactive imaging conjugate may include NK1RL as the NK-1 receptor binding moiety, a linker, and a $^{64}Cu$-labeled NOTA group as the active agent, according to the formula:

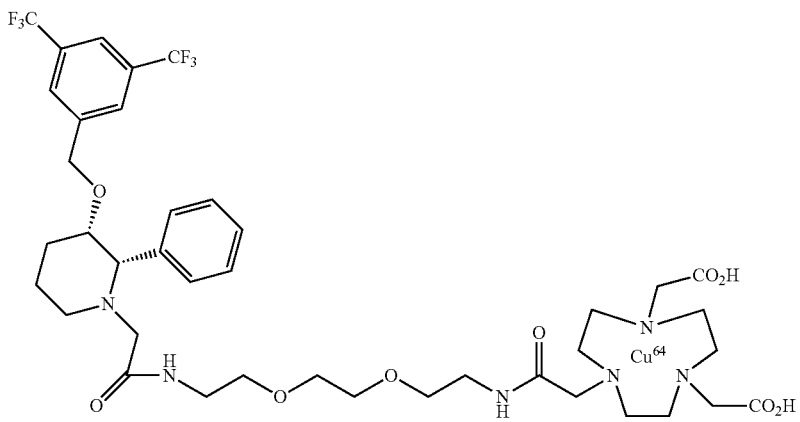 [SMILES: O=C(O)CN1CCN(CC(=O)O)CCN(CC(=O)NCCOCCOCCNC(=O)CN2CCC[C@H](OCc3cc(C(F)(F)F)cc(C(F)(F)F)c3)[C@@H]2c2ccccc2)CC1]

Other compounds may be used in the radioimaging agent and may be labeled with alternative isotopes for PET imaging instead of $^{64}Cu$, including but not limited to, 111-indium, 18-fluorine, 68-gallium, etc. For example, in another embodiment the radioimaging agent may be an $^{111}In$ radio-labeled chelator of 1,4,7,10-tetraazacyclododecane-1, 4,7,10-triacetic acid (DOTA). The radioactive imaging conjugate may include NK1RL as the NK-1 receptor binding moiety, a PEG2 linker, and a $^{111}In$-labeled DOTA group as the active agent, according to the formula:

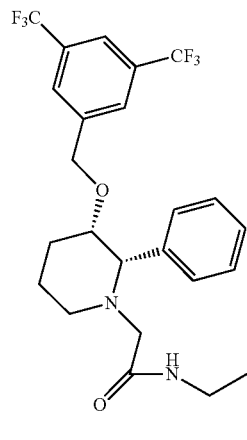

In an example radioimaging conjugate, the NK-1 receptor binding moiety may be NK1RL, the linker group may be a short EC20 linker (e.g., PEG2-based short EC20 linker), and the active agent may be a $^{99m}$Tc radiotag, linked to the chelating portion of the linker group, according to the structure:

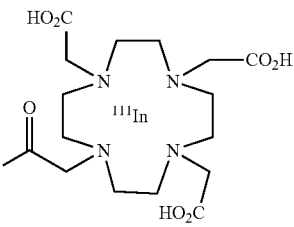

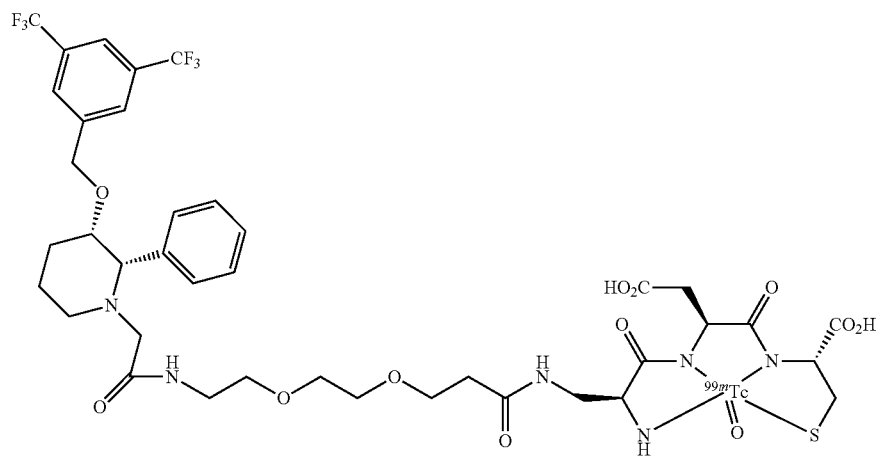

Alternatively, the linker group may be a different short EC20 linker (e.g., PEG36-based short EC20 linker), and the active agent may be $^{99m}$Tc linked to the chelating portion of the linker group, according to the structure:

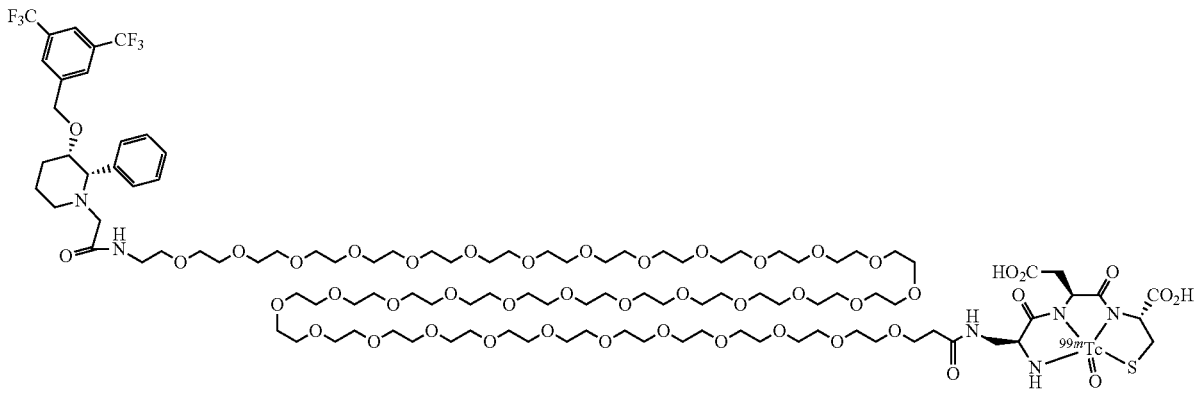

In another example radioimaging conjugate, the NK-1 receptor binding moiety may be NK1RL, the linker group may be PS2 coupled to a short EC20 linker (e.g., PEG2-based short EC20 linker), and the active agent may be a radiotag, such as technetium-99m ($^{99m}$Tc), linked to the chelating portion of the linker group, according to the structure:

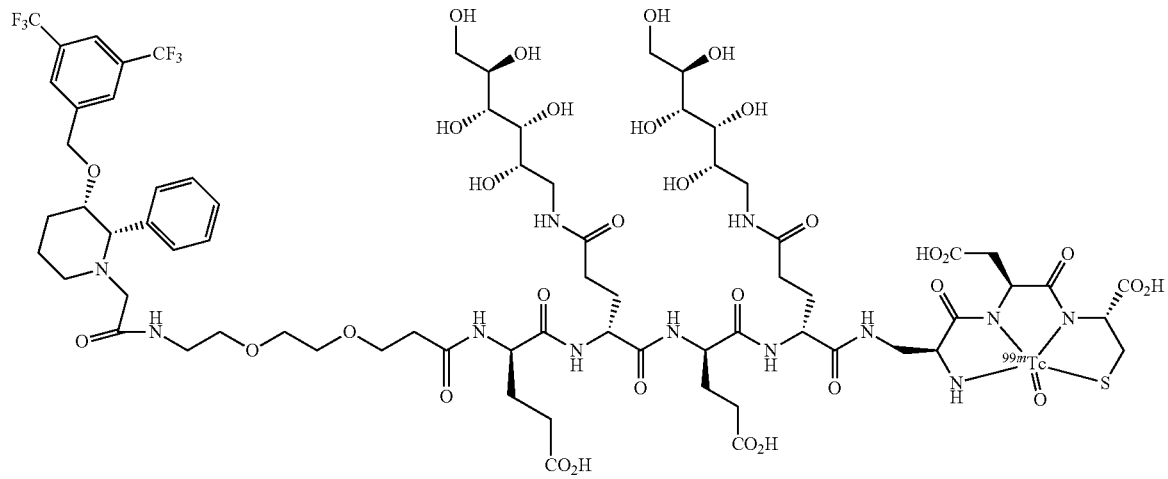

In another set of embodiments, the active agent of the NK-1 receptor-binding agent delivery conjugate may be a fluorescent compound (i.e., fluorescent agent) for use in optical imaging and fluorescence-guided surgery of certain tumors, as may be shown in live tumor-bearing mice in which NK-1 receptors are expressed in tumor tissue. Although most fluorescent agent operate in visible or ultra-violet parts of the spectrum, near infrared (NIR) area may be better suited for fluorescence detection and imaging for scenarios in which high signal-to-noise ratio is important. Therefore, a fluorescent imaging conjugate may include any of a variety of fluorescent agents.

In various embodiments, in tumor uptake in malignant lesions, specificity of the NK-1 receptor-binding agent delivery conjugates to the NK-1 receptor may be confirmed using an active agent containing a fluorescent agent. In particular, fluorescent visualization of the tumor cells may be performed using a fluorescent imaging conjugate, and NK-1 receptor specificity may be established by demonstrating blockade of the fluorescence through administration of excess unlabeled NK-1 receptor binding moiety (e.g., NK1RL). In vivo and in vitro studies of the various embodiment conjugates may be performed using HEK 293 cells which are transduced with TACR1 to express NK-1 receptors.

In another example fluorescent imaging conjugate, the NK-1 receptor binding moiety may be NK1RL, the linker group may be a PEG structure (e.g., PEG36), and the fluorescent agent may be an NIR fluorescent dye S0456, according to the structure:

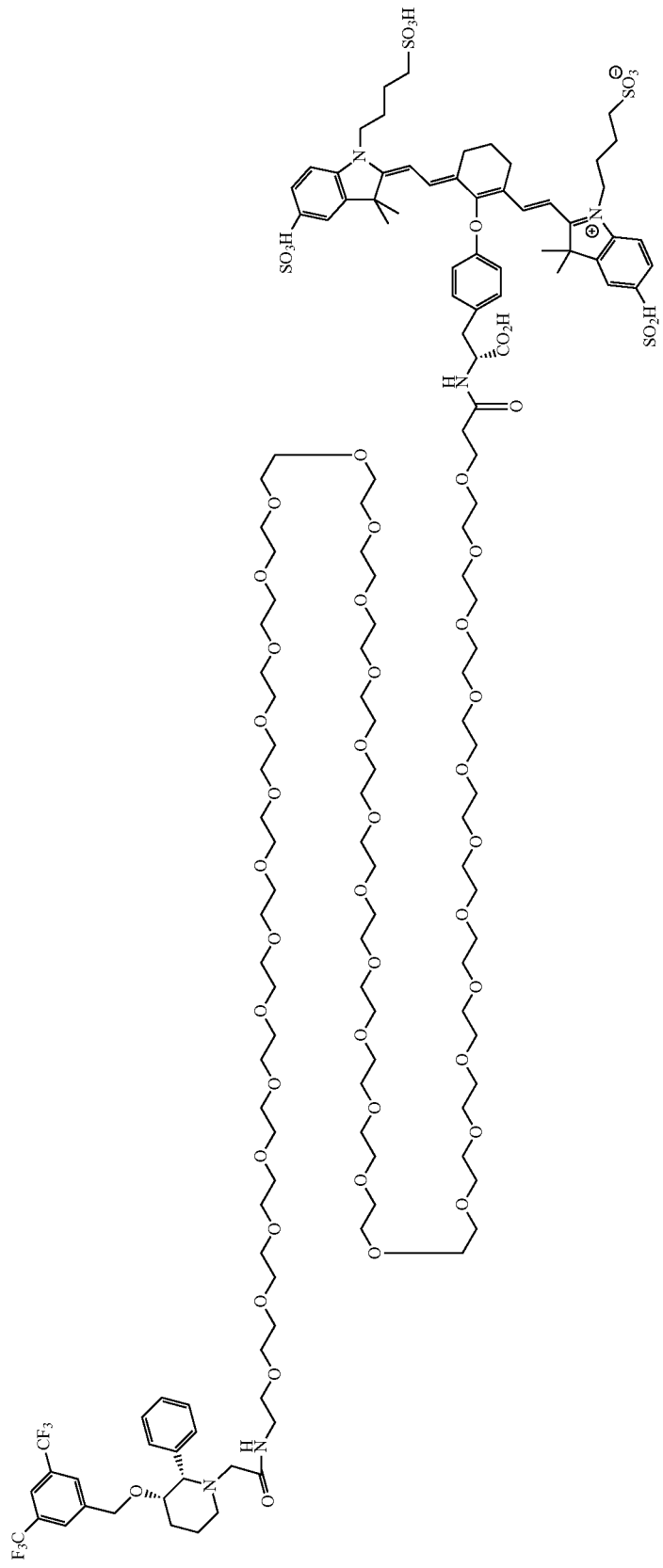

In another example fluorescent imaging conjugate, the NK-1 receptor binding moiety may be NK1RL, the linker group may be the EC20 peptide linker, and the fluorescent agent may be an NIR fluorescent dye LS288-maleimide, according to the structure:

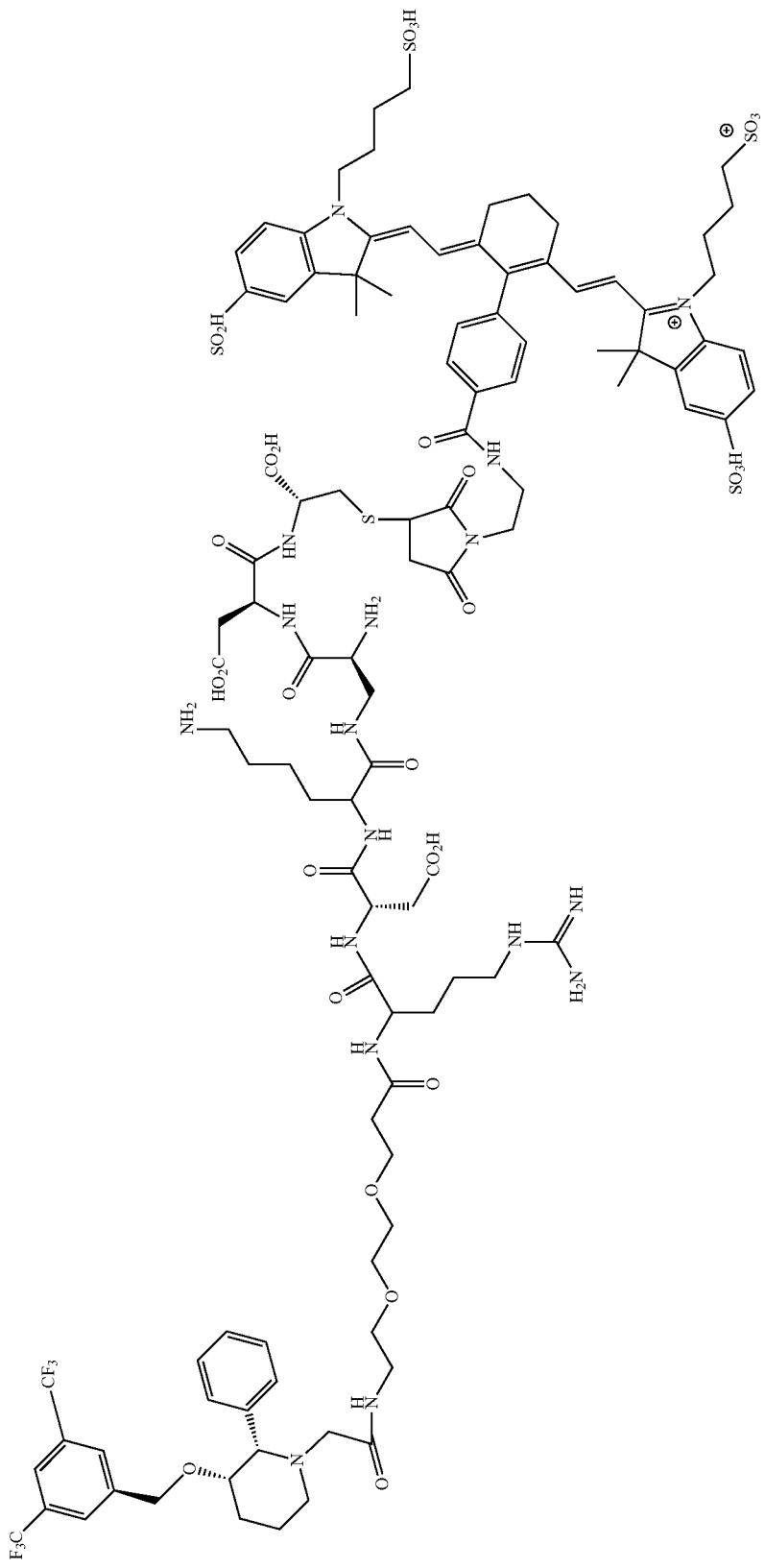

In alternative embodiment fluorescent imaging conjugates, the NK-1 receptor-binding moiety may be a small molecule ligand other than NK1RL. For example, the NK-1 receptor-binding moiety may be a sulfur pentafluoride-containing small molecule ("NK1RL-SF5") according to one of the following structures:

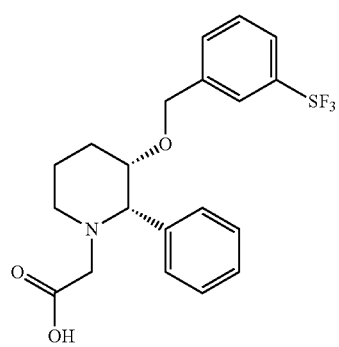

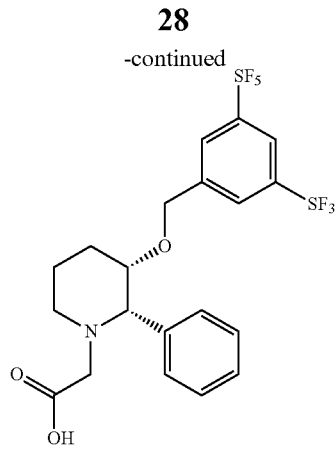

In another example fluorescent imaging conjugate, the NK-1 receptor-binding moiety may be NK1RL-SF5, and the linker group may be PEG2 coupled to a tyrosine-containing peptide, the group being referred to herein as a "tyrosine peptide linker." The active agent may be the NIR fluorescent dye S0456, providing an NK-1 receptor-binding moiety may according to the structure:

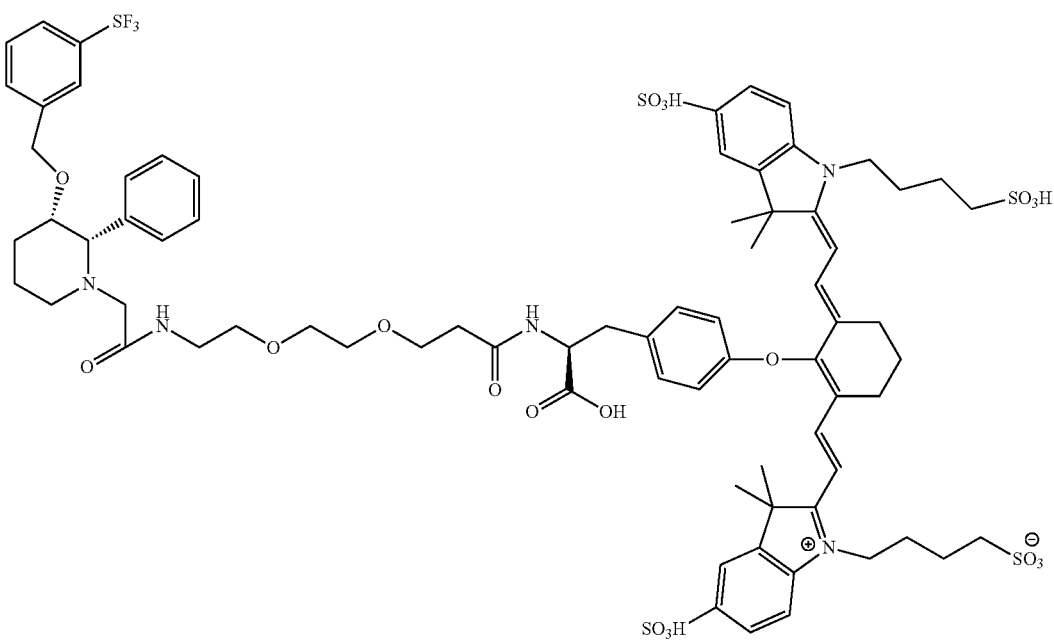

In another example fluorescent imaging conjugate, the NK-1 receptor-binding moiety may be NK1RL-SF5, and the linker group may be a PEG and a peptide group. For example the linker group may be PEG2 coupled to a lysine-containing peptide, with the group being referred to herein as a "lys peptide linker." The active agent may be a rhodamine compound, providing an NK-1 receptor-binding moiety may according to the structure:

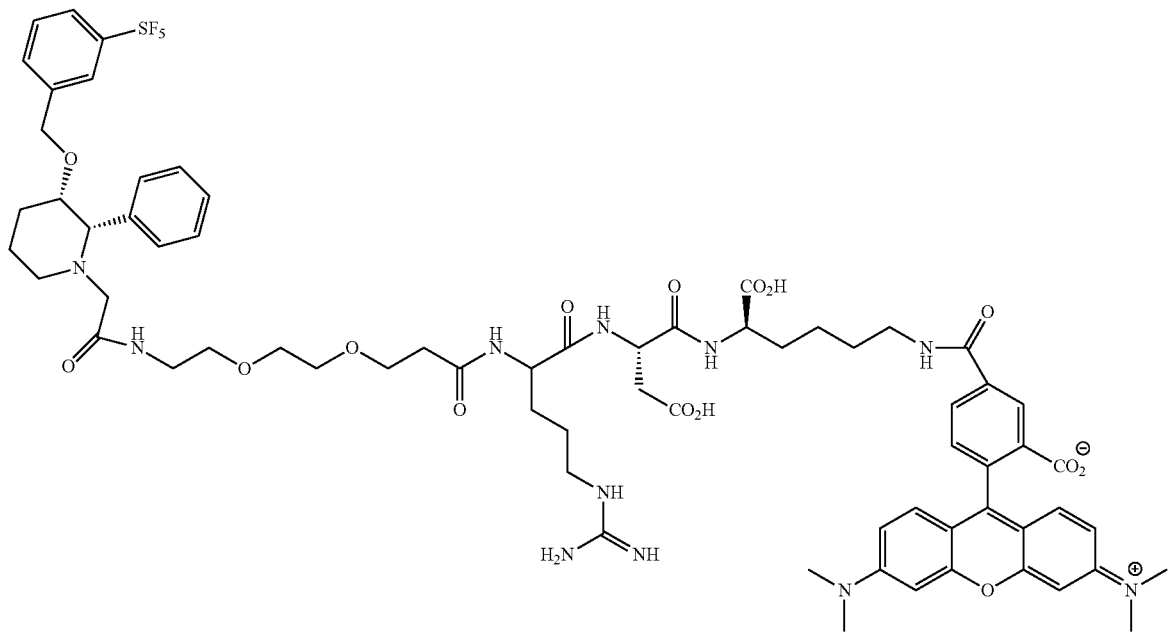

In particular, rhodamine dyes may be used, for example, as a tracer within water to determine the rate and direction of flow and transport. Further, since rhodamines may be detected easily and inexpensively with fluorometers, embodiment fluorescent imaging conjugates in which the active agent in rhodamine may be used in a variety of biotechnology applications (e.g., fluorescence microscopy, flow cytometry, fluorescence correlation spectroscopy, ELISA, etc.) as part of other processes to develop, test, and quantify effectiveness of various conjugates.

Non-limiting examples of fluorophores suitable for use as an active agent in other embodiments may include, without limitation, N,N-dimethyl-4-benzofurazansulfonamide (DBD), 4-(2-Aminoethylamino)-7-(N,N-dimethylsulfamoyl)benzofurazan (DBD-ED), indocyanine green (ICG), a Dylight-700 such as Dylite-700-2B, IR820; 3,3'-Diethylthiatricarbocyanine iodide (DTTCI), LS277, a cypatem, and a coumarin.

In an embodiment, the active agent may be a drug that includes a nitrogen atom, and the linker group may include haloalkylenecarbonyl, optionally substituted with a substituent $X^2$, where the haloalkylenecarbonyl may be bonded to the drug nitrogen to form an amide.

In another embodiment, the active agent may be a drug that includes an oxygen atom, and the linker group may include haloalkylenecarbonyl, optionally substituted with a substituent $X^2$, where the haloalkylenecarbonyl may be bonded to the drug oxygen to form an ester.

In another embodiment, the active agent may be a drug that includes a double-bonded nitrogen atom, and the linker group may include alkylenecarbonylamino and 1-(alkylenecarbonylamino)succinimid-3-yl, where the linker group may be bonded to the drug nitrogen to form a hydrazone.

The drug can include a double-bonded nitrogen atom, and in this embodiment, the releasable linkers can be alkylenecarbonylamino and 1-(alkylenecarbonylamino)succinimid-3-yl, and the releasable linker can be bonded to the drug nitrogen to form an hydrazone.

The various embodiments may be understood by reference to the following non-limiting examples, which are provided by way of illustration only.

Example 1

General

NK-1 receptor-binding agent delivery conjugates were developed for clinical and diagnostic application. In these processes, moisture and oxygen sensitive reactions were carried out under an argon atmosphere. Solid phase peptide synthesis (SPPS) was performed using a standard peptide synthesis apparatus (Chemglass, Vineland, N.J.). Column chromatography was performed with silica gel as the solid phase and TLC was conducted on silica gel TLC plates and visualized under UV light. All peptides and their conjugates were purified by preparative reverse phase (RP)-high performance liquid chromatography (HPLC) and were analyzed by analytical RP-HPLC. $^1$H and $^{13}$C NMR spectra were acquired with Bruker 400 or 500 MHz NMR spectrophotometer and the signals are recorded in ppm with reference to residual CHCl$_3$ (7.27 ppm) or DMSO (2.50 ppm) and data are reported as s=singlet, d=doublet, t=triplet, q=quartet, m=multiplet, b=broad with coupling constants in Hz.

Electrospray ionization-high resolution mass spectrometry (ESI-HRMS) was performed utilizing the appropriate polypropylene glycol standards. Radioactivity was counted on a Packard γ-counter (Packard Instrument Company, Meriden, Conn.). The tumor imaging was performed using a Kodak Image Station (In-Vivo FX, Eastman Kodak Company, New Haven, Conn.).

HEK 293 cell lines stably transfected with neurokinin-1 receptor (NK1R) were utilized. Cell lines were cultured in Dulbecco's modified Eagle's medium (GIBCO) supplemented with 10% fetal bovine serum, G418 disulfate (Sigma Aldrich 400 µg/mL), and 1% penicillin streptomycin at 37° C. in a humidified 95% air 5% CO$_2$ atmosphere.

Athymic male nu/nu mice were purchased from Harlan Laboratories (Indianapolis, Ind.), maintained on normal rodent chow and housed in a sterile environment on a standard 12 h light and dark cycle for the duration of the study. All animal procedures were approved by the Purdue Animal Care and Use Committee (PACUC) in accordance with NIH guidelines.

Synthesis of NK1RL

The NK-1 receptor-binding moiety was an NK-1 receptor ligand (NK1RL) formed from the starting compound (2S,3S)-3-((3,5-bis(trifluoromethyl)benzyl)oxy)-2-phenylpiperidine (L-733,060), a high affinity NK-1 receptor antagonist. The L-733,060 compound was formed according to the literature procedure. Formation of NK1RL from L-733,060 was performed according to the following steps, illustrated in FIG. 1A.

To the (2S,3S)-3-((3,5-bis(trifluoromethyl)benzyl)oxy)-2-phenylpiperidine (1, 0.065 g, 0.16 mmol) in dry THF (1.5 mL), were added tri ethylamine (0.056 mL, 0.4 mmol, 2.5 equiv) followed by tert-butyl-2-bromo acetate (0.035 mL, 0.24 mmol, 1.5 equiv) under $N_2$. The reaction was stirred for 16 hours at room temperature. The reaction was quenched with water and 2% HCl solution and extracted with EtOAc (3×5 mL). The combined organic layers were washed with brine, dried ($Na_2SO_4$), filtered and concentrated and residue was purified by silica-gel column chromatography (hexane: EtOAc, 4:1) to give product, 2 (0.075 g, 92%).

To the ester (0.075 g, 0.14 mmol) in dry $CH_2Cl_2$ was added trifluoroacetic acid (TFA) (20 equiv) and stirred for 4 hours at room temperature. The excess of TFA was removed and diluted with water, extracted with CH2Cl2 (3×5 mL). The combined organic layers were washed with brine, dried ($Na_2SO_4$) and concentrated. The residue obtained was purified by flash silica-gel column chromatography (hexane: EtOAc, 3:7) to give acid, 3 (0.06 g, 90%) as a white solid.

Synthesis of NK1RL-EC20 Peptide Linker

An EC20 peptide linker was created from PEG2 and an amino acid chain (Arg-Asp-Lys-DAP-Asp-Cys). A compound of the linker and NK1 receptor-binding moiety NK1RL (NK1RL-EC20 peptide linker) was synthesized through solid phase peptide synthesis (SPPS) and purified. Synthesis and purification of the NK1RL-EC20 peptide linker compound was performed according to the following steps.

H-Cys(4-methoxytrityl)-Wang resin (150 mg, 0.64 mmol) was swollen in dichloromethane (2×5 mL) and dimethylformamide (DMF) (2×3 mL) while bubbling under argon. After swelling the resin in DMF, a solution of fluorenylmethyloxycarbonyl chloride-aspartic acid-4-tertbutyl ester (Fmoc-Asp(OtBu)-OH) (2.5 equiv), benzotriazol-1-yl-oxytripyrrolidinophosphonium hexafluorophosphate (PyBOP) (2.5 equiv), and N,N-diisopropylethylamine (DIPEA) (5 equiv) in DMF were added. The resulting solution was bubbled under argon for 4 hours and drained, and the resin was washed with DMF (3×5 mL) and isopropyl alcohol (i-PrOH) (3×5 mL). Fmoc deprotection was carried out using 20% piperidine in DMF (3×10 mL) and the resin was washed with DMF (3×5 mL) and i-PrOH (3×5 mL). Ninhydrin tests as described in Kaiser et al. "Color test for detection of free terminal amino groups in the solid-phase synthesis of peptides," Anal Biochem. 1970 April; 34(2): 595-8 ("Kaiser tests") were conducted to assess coupling and deprotection steps. The above sequence was repeated for 5 more coupling steps. Final coupling was done by L-733,060-AcOH (3, 1.5 equiv) under same conditions for 12 hours.

The resin was washed with DMF (3×5 mL) and i-PrOH (3×5 mL) and allowed to dry under nitrogen. The peptide linker was then cleaved from the resin using a mixture of trifluoroacetic acid (TFA):$H_2O$:triisopropylsilane:ethanedithiol cocktail (92.5:2.5:2.5:2.5). The solution was bubbled twice under nitrogen for 15 min, drained, concentrated, and then precipitated by addition of cold diethyl ether. Crude product was collected by centrifugation, washed three more times with cold diethyl ether, dried under vacuum, and then purified by preparative reverse-phase HPLC (Waters, XBridge™ Prep C18, 5 μm; 19×100 mm column, mobile phase A=20 mM ammonium acetate buffer, pH 5, B=acetonitrile, gradient 10-100% B in 30 min, 13 mL/min, λ=280 nm). Pure fractions were analyzed by liquid chromatography mass spectrometry (LC-MS) and low resolution mass spectrometry (LR-MS) and were pooled and lyophilized to furnish a compound of NK1RL-EC20 peptide linker (yield=63.80 mg, 50%. LR-MS (m/z): 1323.53 M+H)+. UV/vis: λmax=254 nm). The ligand-linker compound formed from NK1RL and the EC20 peptide linker is shown in the schematic equation below:

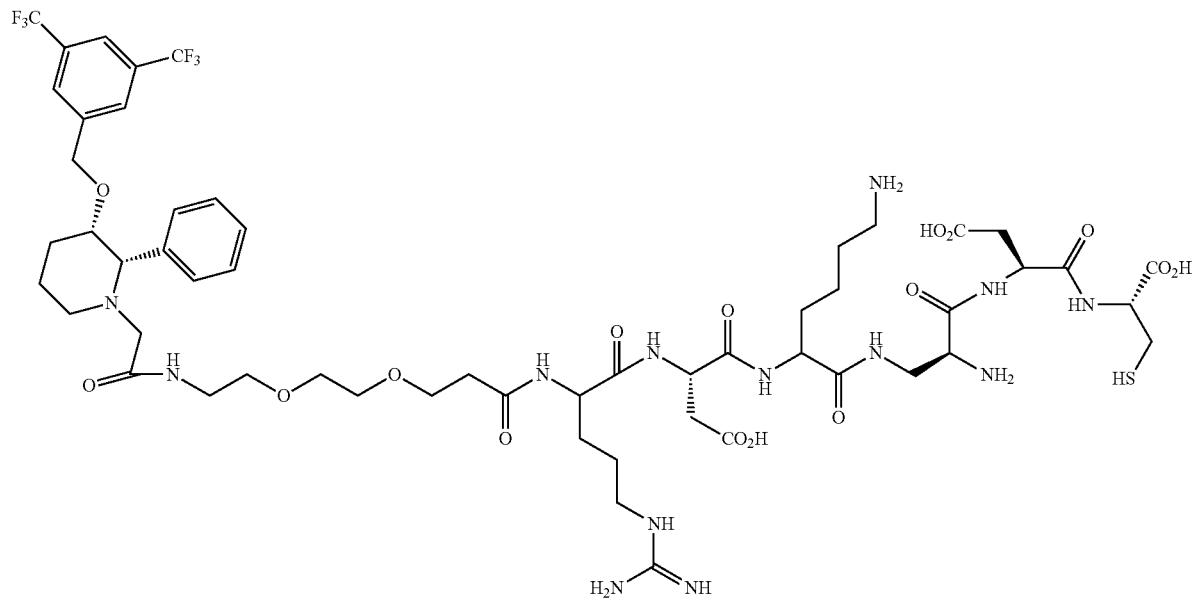 [SMILES: N=C(N)NCCCC(NC(=O)CCOCCOCCNC(=O)CN1CCC[C@H](OCc2cc(C(F)(F)F)cc(C(F)(F)F)c2)[C@@H]1c1ccccc1)C(=O)N[C@@H](CC(=O)O)C(=O)NC(CCCCN)C(=O)NC[C@H](N)C(=O)N[C@@H](CC(=O)O)C(=O)N[C@@H](CS)C(=O)O]

Synthesis of NK1RL-Cys Peptide Linker

A Cys peptide linker was created from PEG2 and an amino acid chain (Arg-Asp-Cys). The ligand-linker compound of NK1RL-Cys peptide linker was synthesized through SPPS with fewer amino acids starting from Cysteine resin and purified. Synthesis and purification of NK1RL-Cys was performed using substantially the same procedure as for NK1RL-EC20 peptide linker.

Synthesis of Drug Conjugates
NK1RL-EC20 Peptide Linker-TubH

To a solution of NK1RL-EC20 peptide linker (2.80 mg, 2.115 μmol) in dry DMSO (0.1 mL) at 0° C., disulfide-activated-TubH (2.0 mg, 2.115 μmol) followed by DIPEA (3 μL, 0.2115 μmol) were added. The reaction mixture was stirred for 3 hours at room temperature, and the crude product was purified by RP-HPLC (Waters, XBridge™ Prep C18, 5 μm; 19×100 mm column, mobile phase A=20 mM ammonium acetate buffer, pH 7, B=acetonitrile, gradient 10-100% B in 30 min, 13 mL/min, λ=280 nm). Pure fractions were analyzed by LC-MS and LR-MS and were pooled and lyophilized to afford NK1RL-EC20 peptide linker-TubH. Yield=3.26 mg, 68%. LR-MS (m/z): 2270.53 (M+H)+. UV/vis: λmax=254 nm.

A schematic equation showing the formation of NK1RL-EC20 peptide linker-TubH is shown below:

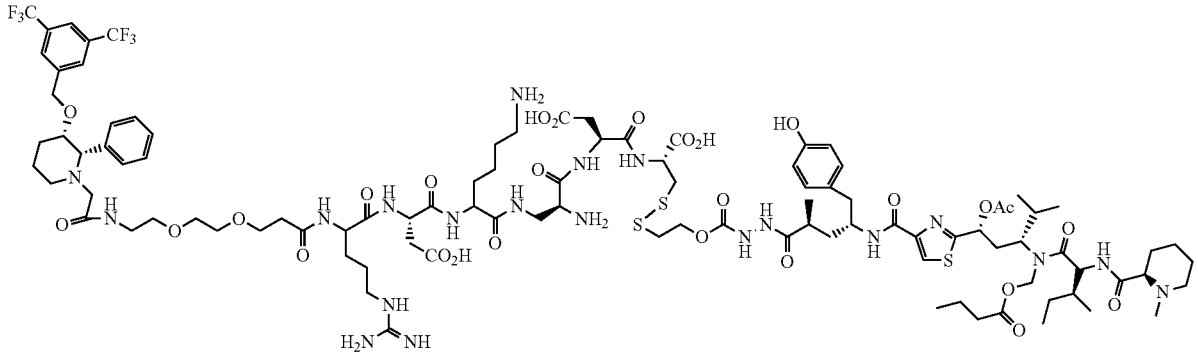 [SMILES: CCCC(=O)OCN(C(=O)C(NC(=O)[C@H]1CCCCN1C)[C@@H](C)CC)[C@H](C[C@@H](OC(C)=O)c1nc(C(=O)N[C@@H](Cc2ccc(O)cc2)C[C@H](C)C(=O)NNC(=O)OCCSSC[C@H](NC(=O)[C@H](CC(=O)O)NC(=O)[C@@H](N)CNC(=O)C(CCCCN)NC(=O)[C@H](CC(=O)O)NC(=O)C(CCCNC(=N)N)NC(=O)CCOCCOCCNC(=O)CN2CCC[C@H](OCc3cc(C(F)(F)F)cc(C(F)(F)F)c3)[C@@H]2c2ccccc2)C(=O)O)cs1)C(C)C]

NK1RL-Cys Peptide Linker-TubH

Further, the same procedural steps were followed using NK1RL-Cys peptide linker discussed above in order to synthesize an NK1RL-Cys peptide linker-TubH compound which was then and purified through RP-HPLC accordingly as described above and characterized.

A schematic equation showing the formation of NK1RL-Cys peptide linker-TubH is shown below:

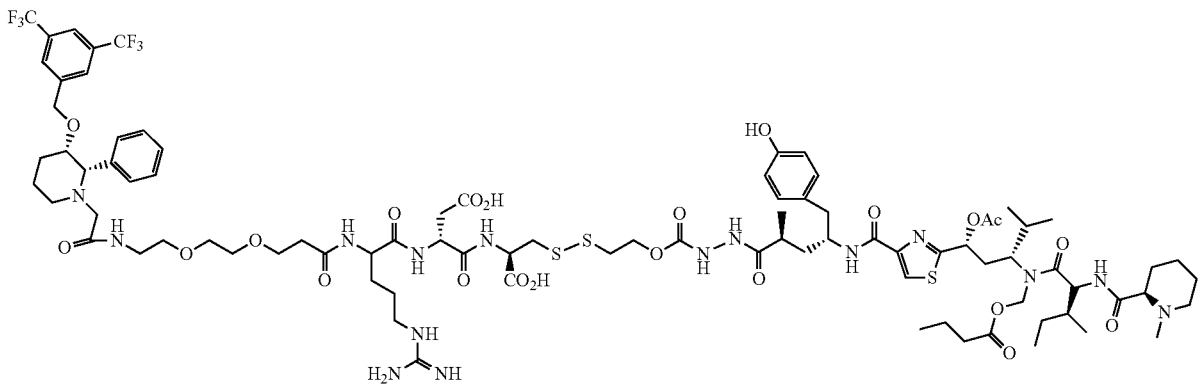 [SMILES: CCCC(=O)OCN(C(=O)C(NC(=O)[C@H]1CCCCN1C)[C@@H](C)CC)[C@H](C[C@@H](OC(C)=O)c1nc(C(=O)N[C@@H](Cc2ccc(O)cc2)C[C@H](C)C(=O)NNC(=O)OCCSSC[C@H](NC(=O)[C@@H](CC(=O)O)NC(=O)C(CCCNC(=N)N)NC(=O)CCOCCOCCNC(=O)CN2CCC[C@H](OCc3cc(C(F)(F)F)cc(C(F)(F)F)c3)[C@@H]2c2ccccc2)C(=O)O)cs1)C(C)C]

NK1RL-EC20 Peptide Linker-DAVBH

To a solution of NK1RL-EC20 linker (1.30 mg, 0.9819 μmol) in dry DMSO (0.1 mL) at 0° C., disulfide-activated-DAVBH (1.16 mg, 1.1782 μmol) followed by DIPEA (2.5 uL, 19.637 μmol) were added. The reaction mixture was stirred for 4 hours at room temperature, and the crude product was purified by RP-HPLC (Waters, XBridge™ Prep C18, 5 μm; 19×100 mm column, mobile phase A=20 mM ammonium acetate buffer, pH 7, B=acetonitrile, gradient 10-100% B in 30 min, 13 mL/min, λ=280 nm). Pure fractions were analyzed by LC-MS and LR-MS and were pooled and lyophilized to afford NK1RL-EC20 peptide linker-DAVBH (yield=1.40 mg, 65%. LR-MS (m/z): 2195.43 (M+H)+. UV/vis: λmax=254 nm).

A schematic equation showing the formation of NK1RL-EC20 peptide linker-DAVBH is shown below:

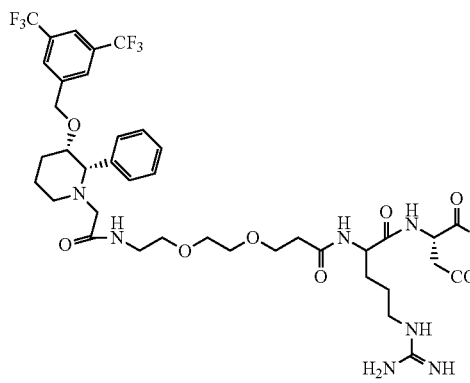

NK1RL-Cys Peptide Linker-DAVBH

Further, the same procedural steps were followed using NK1RL-Cys peptide linker discussed above in order to synthesize an NK1RL-Cys peptide linker-DAVBH conjugate which was then and purified through RP-HPLC accordingly as described above and characterized.

A schematic equation showing the formation of NK1RL-Cys peptide linker-DAVBH is shown below:

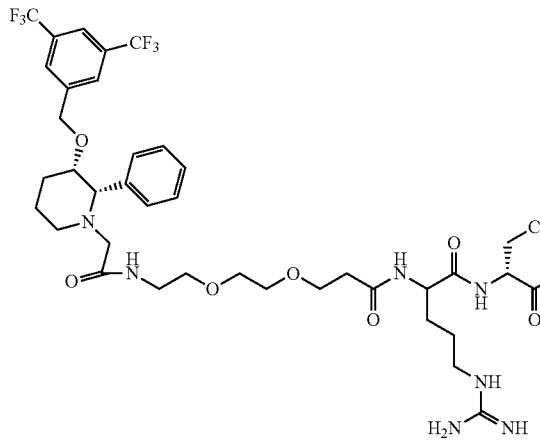

Cytotoxicity Study ($IC_{50}$) for Drug Conjugates

HEK 293 NK1R cells (50,000 cells/well) were seeded into 24 well plates (BD Purecoat Amine, BD Biosciences) and allowed to grow to form monolayer over 24 to 48 hours. The old medium was replaced with fresh medium (0.5 mL) containing increasing concentrations of drug conjugates (either targeted or non-targeted NK1RL, and free-ligand) and cells were incubated for an additional 2 hours at 37° C. Cells were washed (3×0.5 mL) with fresh medium and incubated in fresh medium (0.5 mL) for another 66 hours at 37° C. The spent medium in each well was replaced with fresh medium (0.5 mL) containing [3H]-thymidine (1 mCi/mL), and the cells were incubated for additional 4 hours at 37° C. to allow [3H]-thymidine incorporation. The cells were then washed with medium (2×0.5 mL) and treated with 5% trichloroacetic acid (0.5 mL) for 10 min at room temperature. The trichloroacetic acid was replaced with 0.25 N NaOH (0.5 mL), cells were transferred to individual scintillation vials containing Ecolume scintillation cocktail (3.0 mL), mixed well to form homogeneous liquid and counted in a liquid scintillation analyzer. $IC_{50}$ values were calculated by plotting %[3H]-thymidine incorporation versus log concentration of drugs (targeted and non-targeted) using in GraphPad Prism 4.

In Vivo Studies for Drug Conjugates

Four- to six-week old male nu/nu mice were maintained on a standard 12 hours light-dark cycle and fed on normal mouse chow for the duration of the experiment and were inoculated subcutaneously on their shoulders with HEK 293-NK1R cells (5.0×106 cells/mouse in 50% HC Matrigel) using a 25-gauge needle. Growth of the tumors was measured in two perpendicular directions every 2 days using a caliper, and the volumes of the tumors were calculated as 0.5×L×W2 (L=measurement of longest axis, and W=axis perpendicular to L in millimeters). Experiments on live mice involved at least five mice per group and animals were treated with therapeutic drug conjugates (1.6 μmol/kg of body weight) in saline (100 μL) for three weeks, 3 doses per week (M/W/F), when the tumors reached 75-130 mm³ volume (~3 weeks): Tumor volumes and body weights were also measured at each dose. In vivo efficacy was evaluated by plotting tumor volume versus days and % of weight loss/gain versus days on therapy. Three weeks after treatment, the animals were dissected and selected tissues were preserved in formalin for histopathology studies. H&E stained slides for microscopic evaluation were prepared from submitted fixed tissues.

Figure 1B:
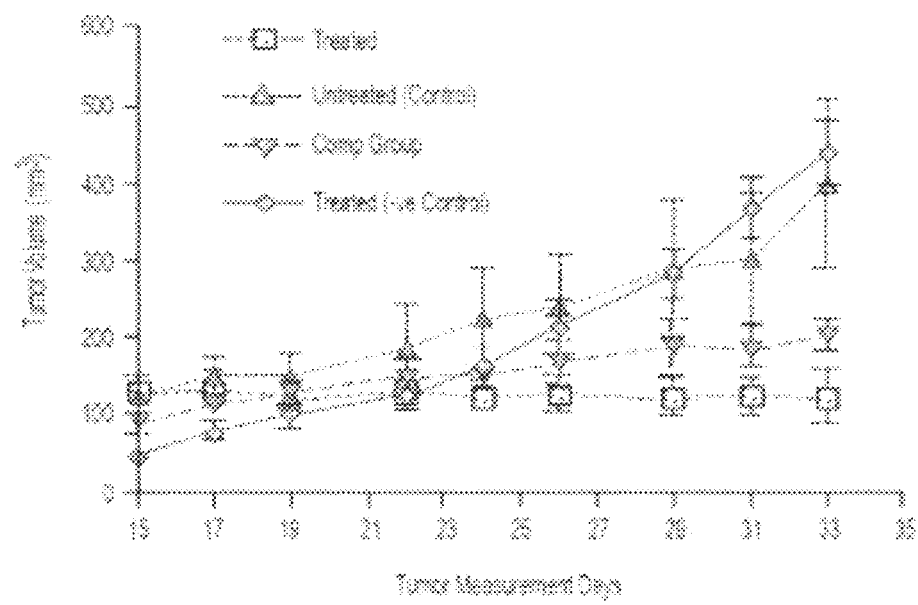
FIG. 1B provides in vivo mice therapeutic data for HEK 293-NK1R tumor xenograft models showing behavior of tumor volumes from the NK1R-EC20 peptide linker-TubH conjugate.
Figure 1C:
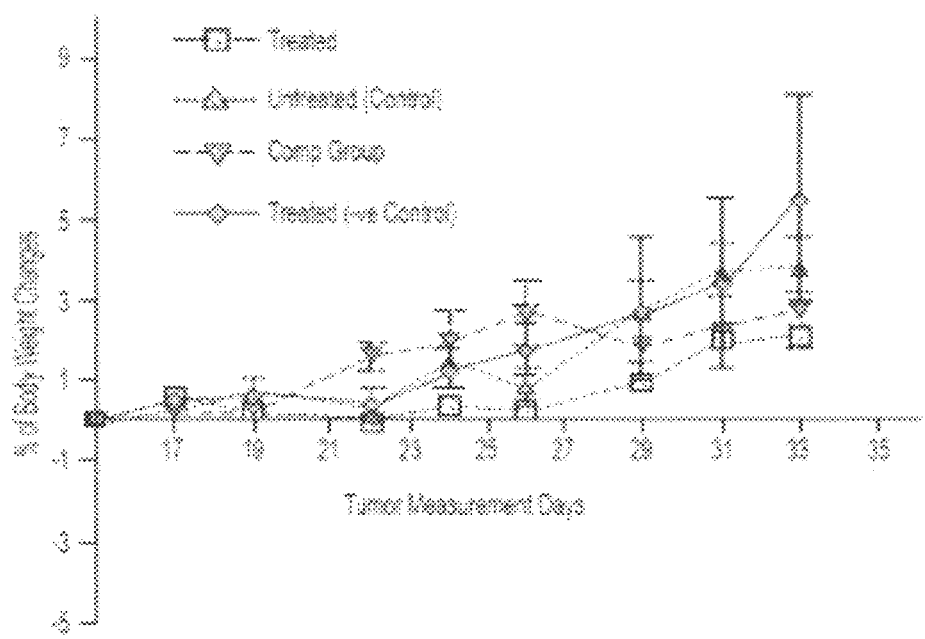
FIG. 1C provides in vivo mice therapeutic data on HEK 293-NK1R tumor xenograft models showing behavior body weights during the therapy shown in FIG. 1B.

FIG. 1B provides in vivo mice therapeutic data for HEK 293-NK1R tumor xenograft models showing behavior of tumor volumes from the NK1R-EC20 peptide linker-TubH conjugate. FIG. 1C provides in vivo mice therapeutic data on HEK 293-NK1R tumor xenografts model showing behavior body weights during the therapy shown in FIG. 1B.

Example 2

Figure 2:
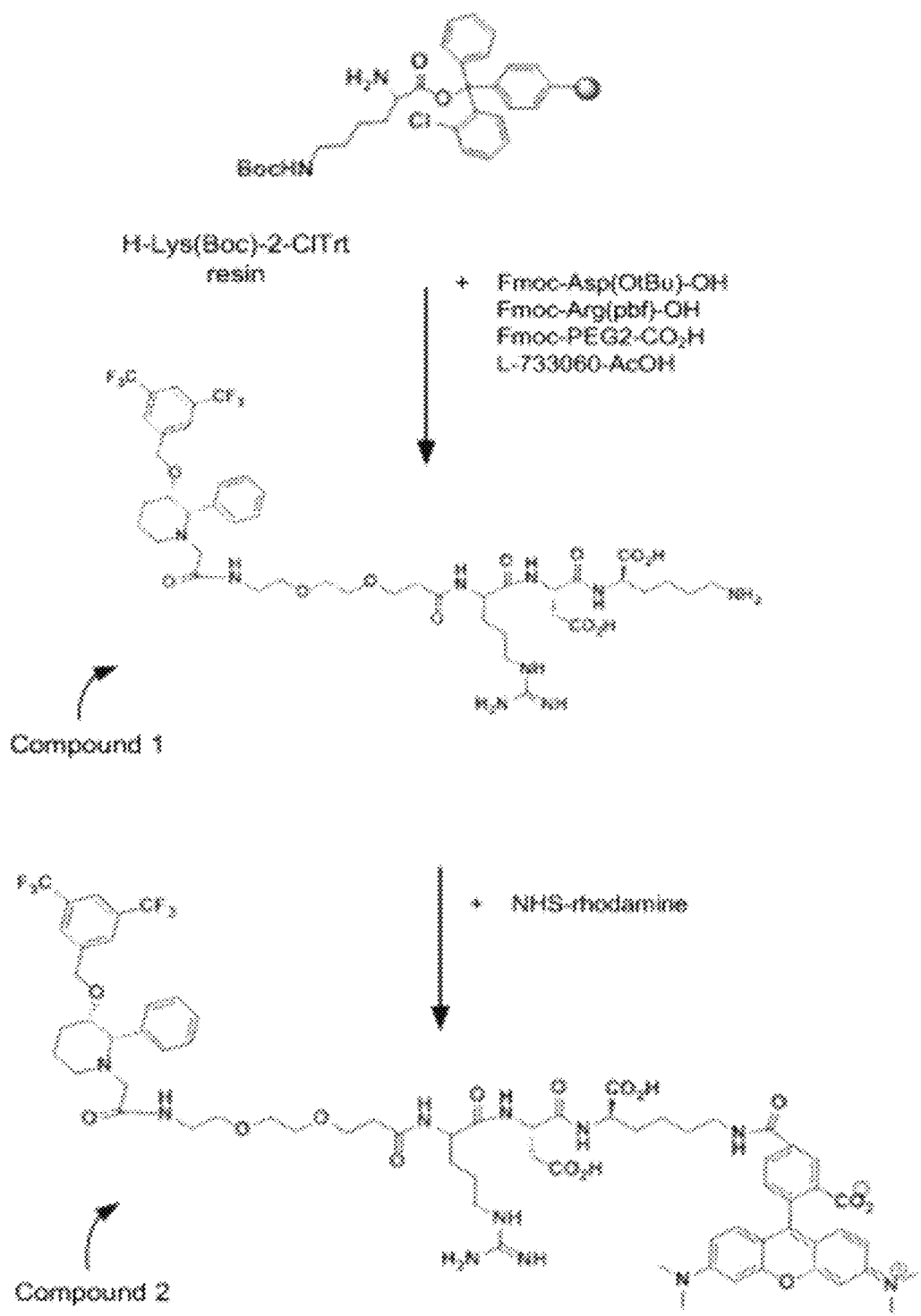
FIG. 2 is a schematic reaction equation illustrating the synthesis of an NK1RL-Lys peptide-rhodamine conjugate.

As illustrated in FIG. 2, synthesis of NK1RL-Lys peptide linker-rhodamine conjugate was carried out by synthesizing the NK1RL-Lys peptide linker, to which NHS-rhodamine was added. Specifically, NK1RL-Lys peptide linker-rhodamine conjugate synthesis was performed using the following steps.

Synthesis of NK1RL-Lys Peptide Linker

H-Lys (Boc)-2-Cl-Trt resin (80 mg, 0.75 mmol) was swollen in dichloromethane (DCM) (2×5 mL) and DMF (2×3 mL) while bubbling under argon. A solution of Fmoc-Asp(OtBu)-OH (2.5 equiv), PyBOP (2.5 equiv), and DIPEA (5 equiv) in DMF was added. The resulting solution was bubbled under argon for 3 hours and drained, and the resin was washed with DMF (3×5 mL) and i-PrOH (3×5 mL). Fmoc deprotection was carried out using 20% piperidine in DMF (3×5 mL). The deprotection solution was removed, and the resin was washed again with DMF (3×5 mL) and i-PrOH (3×5 mL). Kaiser tests were conducted to assess coupling and deprotection steps. The same procedure were followed for Fmoc-arginine-(2,2,4,6,7-pentamethyl-2,3-dihydrobenzofuran-5-sulfonyl) ester (Fmoc-Arg(pbf)-OH), Fmoc-PEG2-CO$_2$H, and NK1L (L-733,060-acetic acid) couplings, with the reaction being bubbled over night for NK1L. The resin was washed with DMF (3×5 mL) and i-PrOH (3×5 mL) and allowed to dry under nitrogen. The NK1L-peptide linker was then cleaved from the resin using a mixture of 95% trifluoroacetic acid (TFA), 2.5% H$_2$O and 2.5% triisopropylsilane (TIPS). The solution was bubbled three times under nitrogen for 15 min, drained, concentrated, and then precipitated by addition of cold diethyl ether. Crude product was collected by centrifugation, washed three more times with cold diethyl ether, dried under vacuum, and then purified by preparative reverse-phase HPLC (Waters, XBridge™ Prep C18, 5 µm; 19×100 mm column, mobile phase A=20 mM ammonium acetate buffer, pH 7, B=acetonitrile, gradient 0-80% B in 30 min, 13 mL/min, λ=254 nm). Pure fractions were analyzed by LC-MS (XBridge™ RP18, 3.5 µm; 3.0×50 mm column) and low resolution electrospray ionisation mass spectrometry (LR-ESIMS), and were pooled and lyophilized to furnish NK1RL-Lys peptide linker (Compound 1 in FIG. 2).

Synthesis of NK1RL-Lys Peptide Linker-Rhodamine Conjugate

The purified NK1RL-Lys peptide linker (Compound 1 in FIG. 2) was coupled with NHS-rhodamine by stirring 1:1.2 ratios of Compound 1 to NHS-rhodamine in dry DMSO, DIPEA under argon for 12 hours at room temperature. The resulting material was purified using RP-HPLC (mobile phase A=20 mM ammonium acetate buffer, pH 7, B=acetonitrile, gradient 0-80% B in 30 min, 13 mL/min, 7λ=280 nm). Pure fractions were combined, concentrated under vacuum, and lyophilized to yield the product, NK1RL-Lys peptide linker-rhodamine (Compound 2 in FIG. 2). The NK1RL-Lys peptide linker-rhodamine conjugate is a reddish solid, was analyzed by LC-MS and LR-ESIMS.

Synthesis of NK1RL-EC20 Peptide Linker-LS288 Conjugate

Figure 3:
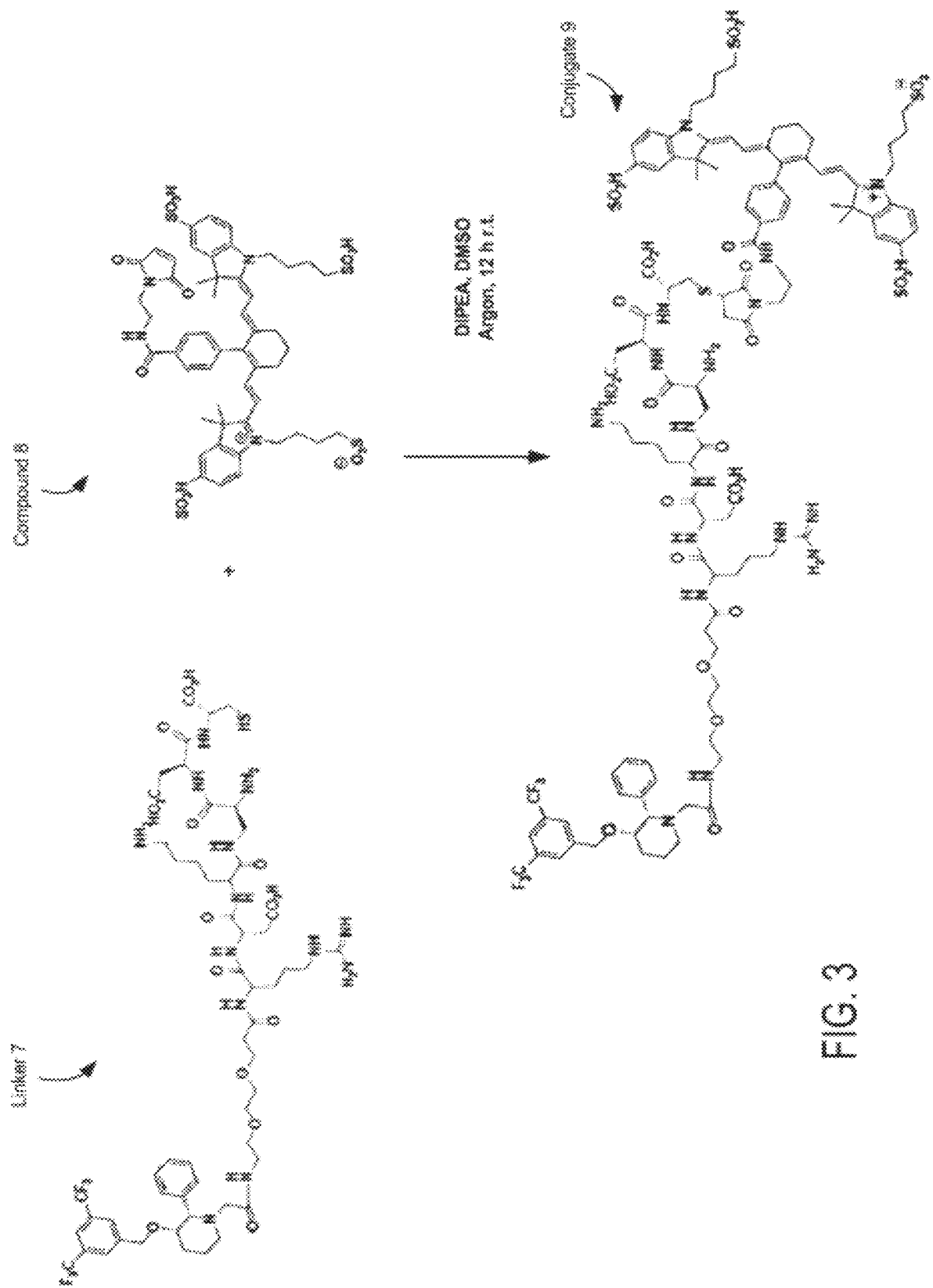
FIG. 3 is a schematic reaction equation illustrating the synthesis of an NK1RL-EC20 peptide-LS288-maleimide conjugate.

NK1RL was synthesized as the NK-1 receptor-binding moiety as discussed above. Synthesis of NK1RL-EC20 peptide linker-LS288 conjugate is illustrated in FIG. 3, and was carried out using the following steps.

To the NK1RL-EC20 peptide linker (Linker 7) in dry DMSO were added LS288-maleimide (Compound 8) followed by DIPEA under argon atmosphere at room temperature. The reaction mixture was stirred for overnight at room temperature. The product was precipitated by addition of isopropanol and collected by centrifugation. The crude product was purified by preparative reverse phase HPLC using a mobile phase of A=20 mM ammonium acetate buffer, pH 7; B=acetonitrile; gradient 0-50% B in 30 min, 13 ml/min, λ=280 nm. Pure fractions were analyzed by LC-MS and LR-MS and were pooled and lyophilized to furnish NK1RL-EC20 peptide linker-LS288 conjugate (Conjugate 9).

Fluorescent Confocal Microscopy Imaging

HEK 293-NK1R cells (50,000 cells/well in 0.5 mL) were seeded into confocal microwell plate (Lab-Tek, Chambered #1.0 Borosilicate Coverglass) and allowed cells to form monolayers over 24 hours. Spent medium was replaced with fresh medium containing NK1RL-Lys peptide linker-rhodamine (25 nM) in the presence or absence of 100-fold excess free ligand and cells were incubated for 1 hour at 37° C. After washing with fresh medium (3×0.5 mL), confocal images were acquired using a confocal microscopy (FV 1000, Olympus).

Figure 4:
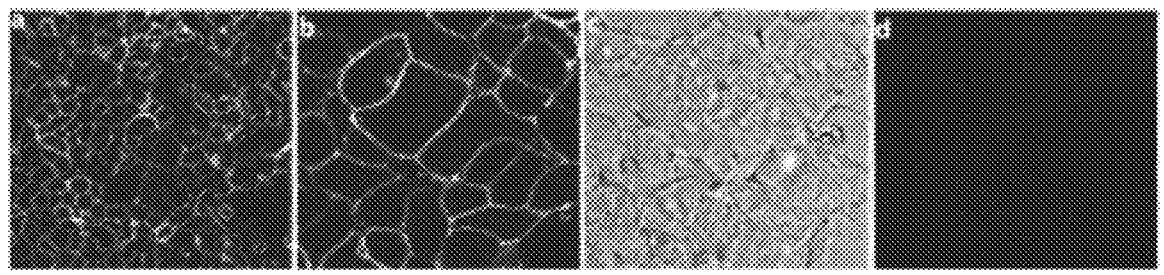
FIG. 4 is a set of confocal microscopy images showing in vitro binding of NK1RL-Lys peptide linker-rhodamine to HEK 293-NK1R cells.

FIG. 4 shows resulting images from the binding studies of the NK1RL-Lys peptide linker-rhodamine conjugate to HEK 293-NK1R cells. Specifically, the images show incubation of cells for 1 hour at 37° C. in the absence (a) and presence (d) of 100-fold excess of competing agent (NK1RL alone) to the conjugate at 25 nM concentration. The images in (b) are 3× magnification from (a), and in (c) are 3× magnification of white light.

Flow Cytometric Analysis

Procedure

HEK 293 NK1R cells were seeded into a T75 flask and allowed to form a monolayer over 48 hours. After trypsin digestion, released cells were transferred into centrifuge tubes (1×105 cells/tube) and centrifuged. The medium was replaced with fresh medium containing NK1RL-Rhod (25 nM) in the presence or absence of 100-fold excess unlabeled NK1RL ligand and incubated for 1 h at 37° C. After rinsing with fresh medium (3×0.5 mL), cells were re-suspended in PBS (0.5 mL) and cell bound fluorescence was analyzed (40,000 cells/sample) using a flow cytometer. Untreated HEK 293-NK1R cells in PBS served as a negative control.

Determination of Binding Affinity and Specificity

HEK 293 NK1R cells (50,000 cells/well) were seeded into 24 well plates (BD Purecoat Amine, BD Biosciences) and allowed to grow to confluence over 48-72 hours. Spent medium in each well was replaced with 0.5 mL of fresh medium containing 0.5% bovine serum albumin and increasing concentrations of the NIR dye conjugates in the presence or absence of 100-fold excess of competing ligand (i.e., L-733,060). After incubation for 1 hour at 37° C., cells were rinsed with incubation solution (2×0.5 mL) to remove unbound fluorescence and dissolved in 0.5 mL of 1% aqueous sodium dodecyl sulfate (SDS). Cell associated fluorescence was then determined by measuring maximum emission of the resulting solution by transfer to a quartz cuvette upon excitation of each dye (rhodamine/LS288) at 545/755 nm using an Agilent Technologies Cary Eclipse fluorescence spectrophotometer. Experiments were performed in triplicate. The conjugate's dissociation constant (KD) was calculated from a lot of cell bound fluorescence emission (a.u.) versus the concentration of targeted NIR probe added using the GraphPad Prism 4 program and assuming a non-cooperative single site binding equilibrium.

Figure 5:
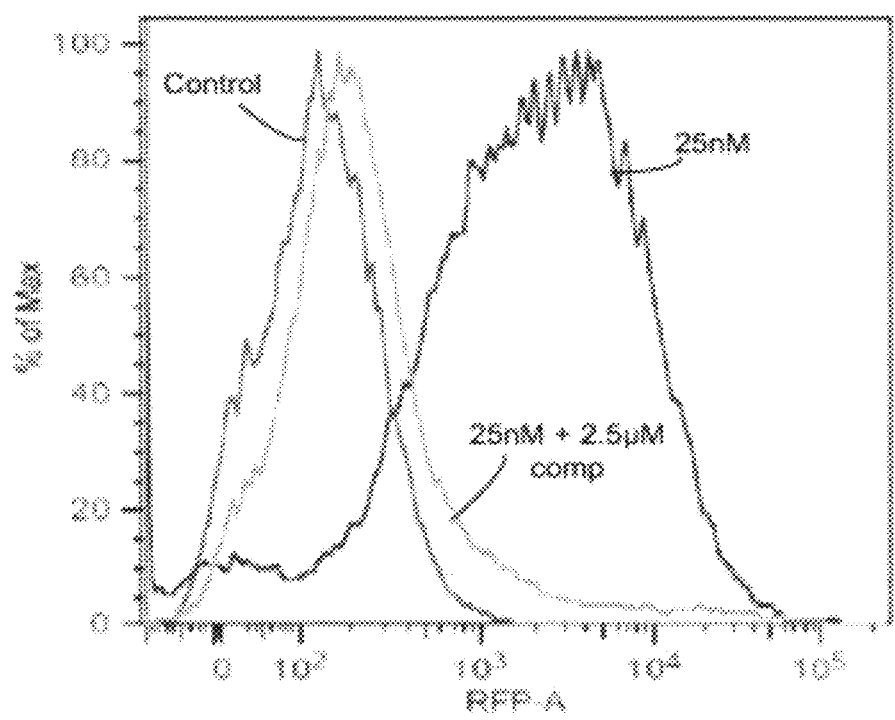
FIG. 5 is a graph showing the binding of NK1RL-Lys peptide rhodamine to HEK 293-NK1R cells by flow cytometry.
Figure 6A:
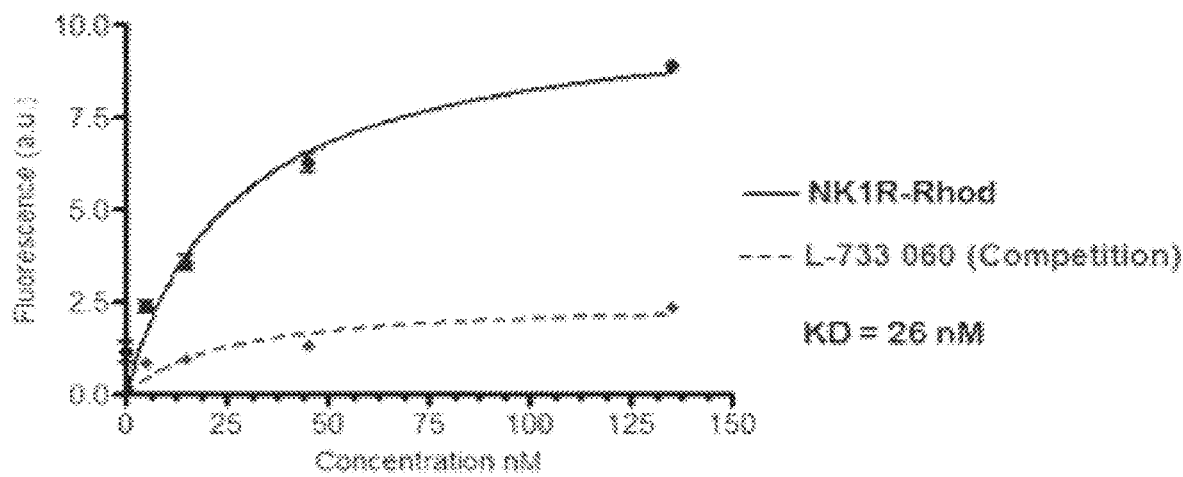
FIGS. 6A and 6B are graphs showing binding affinity of two fluorescent imaging conjugates in cultured HEK 293-NK1R cells expressing NK-1 receptor.
Figure 6B:
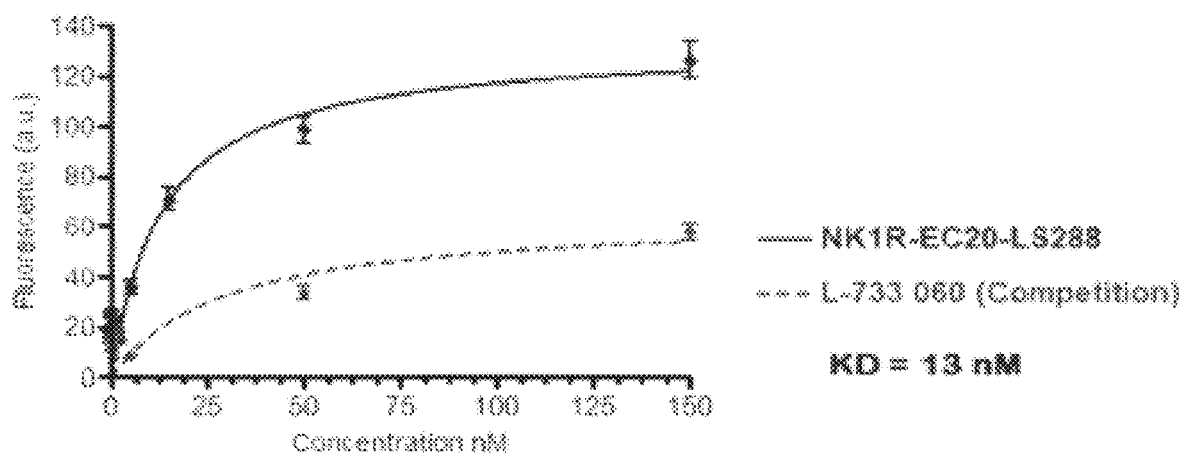

FIG. 5 shows the binding of NK1RL-Lys peptide linker-rhodamine to HEK 293-NK1R cells by flow cytometry. FIG. 6A shows the binding affinity of the NK1RL-Lys peptide linker-rhodamine conjugate in cultured HEK 293-NK1R cells expressing NK-1 receptor. FIG. 6B shows the binding affinity of the NK1RL-EC20 peptide linker-LS288-maleimide conjugate.

In Vivo Assays

Implantation of Subcutaneous Tumors Using HEK 293-NK1R Cells

Six week old male athymic nu/nu mice (Harlan Laboratories, IN) were inoculated subcutaneously on their shoulders with HEK 293 NK1R cells (5.0×106 cells/mouse in 50% HC Matrigel) using a 25-gauge needle. Growth of the tumors was measured in two perpendicular directions every 2 days using a caliper, and the volumes of the tumors were calculated as 0.5×L×W2 (L=measurement of longest axis, and W=measurement of axis perpendicular to L in millimeters). Animals were imaged when the tumors reached 300-500 mm³ volume (~2-3 weeks). Experiments on live mice involved at least four mice per group. Imaging was then performed as described below.

Fluorescence Imaging and Analysis of Mice

Tumor bearing mice were treated via tail vein (i.v) injection with 10 nmol of dye conjugate with 100 fold excess competition [three groups (one is dye, two is competition and three is –ve control (KB tumor) groups), 4 mice/group] and imaged 2 hours post injection using a Caliper IVIS Lumina II Imaging station coupled to ISOON5160 Andor Nikon camera equipped with Living Image Software Version 4.0. The 2 hour time point for imaging was chosen based on data from previous experiments showing that a radio labeled conjugate of NK1 yielded the highest tumor-to-background ratio at this time point. The settings were as follows: lamp level, high; excitation, 745 nM; emission, ICG; epi illumination; binning (M) 4; FOV, 12.5; f-stop, 4; acquisition time, 1 second. After completion of whole body imaging, animals were dissected and selected organs were collected and imaged again for complete biodistribution. All organs were preserved in 25 mL of formalin in preparation for submission to the Purdue Histology & Phenotyping Laboratory for hematoxylin and eosin staining.

Figure 6C:
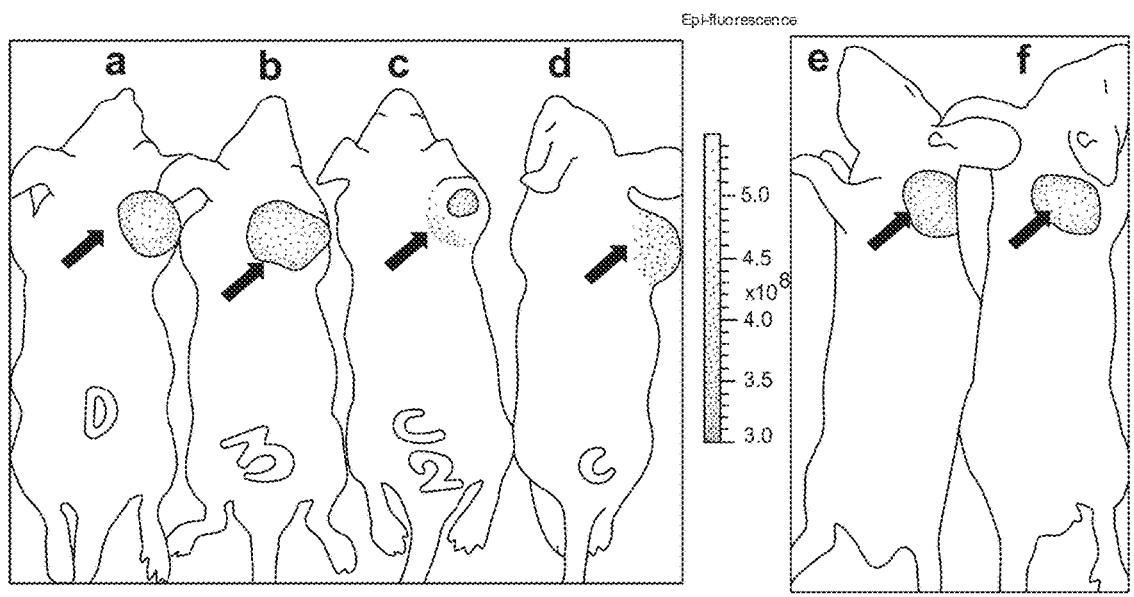
FIG. 6C is a set of images showing (a-b) HEK 293-NK1R tumor xenograft model mice treated with conjugates in which LS288 is the active agent, (c-d) blocking images for the HEK 293-NK1R tumor xenograft model mice with the treatment in a-b, and (e-f) NK1R-negative tumor xenograft model mice treated with conjugates in which LS288 is the active agent.
Figure 6D:
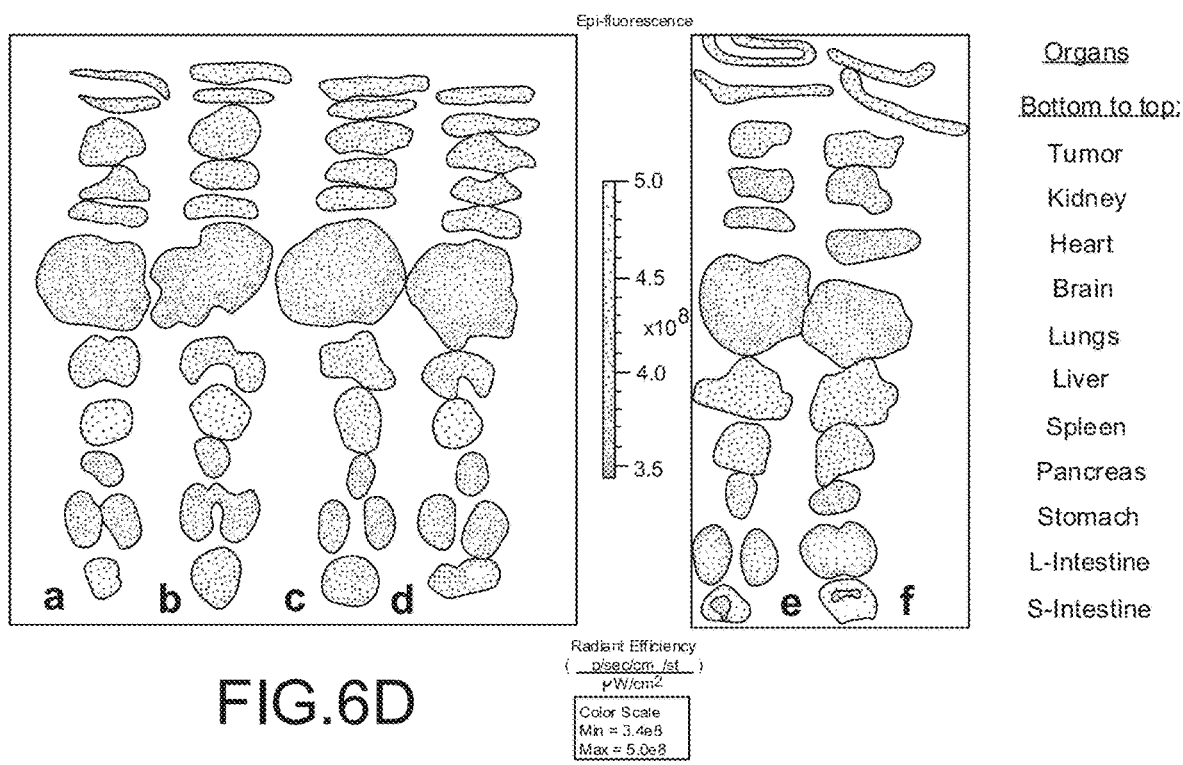
FIG. 6D is a biodistribution study of the mice imaged in FIG. 6C.

FIG. 6C shows (a-b) HEK 293-NK1R tumor xenograft model mice treated with conjugates in which LS288 is the active agent, (c-d) blocking images for the HEK 293-NK1R tumor xenograft model mice with the treatment in a-b, and (e-f) NK1R-negative tumor xenograft model mice treated with conjugates in which LS288 is the active agent. FIG. 6D is a biodistribution study of the imaged mice in FIG. 6C.

Example 3

Synthesis of the NK1RL-EC20 Peptide Linker-$^{99m}$Tc Conjugate

A solution of sodium pertechnetate (1.0 mL, 15 mCi) was added to a vial containing a lyophilized mixture of NK1RL-EC20 peptide linker (0.178 mg), sodium α-D-glucoheptanoate dehydrate (80 mg), stannous chloride dihydrate (0.8 mg), and sufficient NaOH to achieve pH of 7.2 upon rehydration with water. After adding sodium pertechnetate (15 mCi), the vial was heated in a boiling water bath for 18 minutes and then cooled to room temperature before use. The labeling efficiency, radiochemical purity, and radiochemical stability were analyzed by RP-HPLC.

In Vitro Studies

Figure 7A:
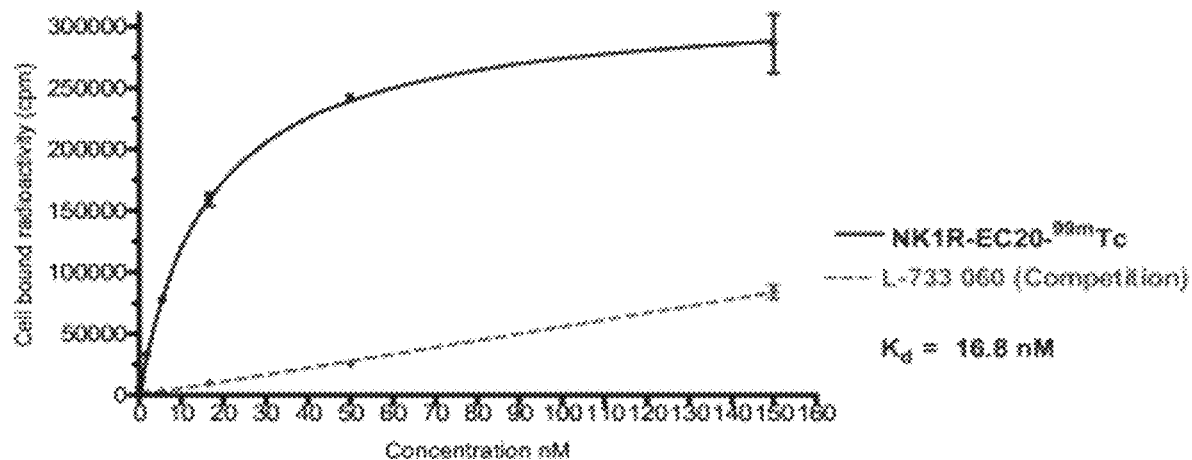
FIG. 7A is a plot showing the radioactivity binding affinity of an NK1RL-EC20 peptide linker-$^{99m}$Tc conjugate versus concentration of the conjugate in cells.

HEK 293 NK1R cells (50,000 cells/well) were seeded into 24 well plates (BD Purecoat Amine, BD Biosciences) and allowed to grow to confluence over 48-72 hours. Spent medium in each well was replaced with 0.5 mL of fresh medium containing 0.5% bovine serum albumin and increasing concentrations of NK1RL-EC20 peptide linker-$^{99m}$Tc in the presence or absence of 100-fold excess of competing ligand, i.e., L-733,060. After incubation for 1 hour at 37° C., cells were rinsed with incubation solution (3×0.5 mL) to remove unbound radioactive material and cells were dissolved in 0.25 M NaOH aqueous (0.5 mL) solution. The dissolved cells were transferred into individual γ-counter tubes and radioactivity was counted using a γ-counter. The binding constant (Kd) was calculated by plotting bound radioactivity versus the concentration of targeted radiotracer using GraphPad Prism 4 program, illustrated in FIG. 7A.

In Vivo Studies

Four- to six-week old male nu/nu mice were inoculated subcutaneously on their shoulders with HEK 293 NK1R cells (5.0×106 cells/mouse in 50% HC Matrigel) using a 25-gauge needle. Growth of the tumors was measured in two perpendicular directions every 2 days using a caliper, and the volumes of the tumors were calculated as 0.5×L×W2 (L=measurement of longest axis, and W=axis perpendicular to L in millimeters). Animals were treated with NK1RL-EC20 peptide linker-$^{99m}$Tc (1.34 nmol, 150 μCi) in saline (100 μL) when the tumors reached 300-500 mm3 volume (~3 weeks). Experiments on live mice involved at least four mice per group, animals were sacrificed by $CO_2$ asphyxiation at different time points as described below. Images were acquired by a Kodak Imaging Station in combination with CCD camera and Kodak molecular imaging software (version 4.0) (radioimages: illumination source=radio isotope, acquisition time=2 and 4 min, f-stop=0, focal plane=5, FOV=162.5, binning=4; White light images: illumination source=white light transillumination, acquisition time=0.175 seconds, f-stop=11, focal plane=5, FOV=162.5 with no binning).

Following imaging, animals were dissected and selected tissues were collected into pre-weighed γ-counter tubes. Radioactivity of pre-weighed tissues and NK1RL-EC20 peptide linker-$^{99m}$Tc (1.34 nmol, 150 μCi) in saline (100 μL) was counted in a γ-counter. CPM values were decay corrected and results were calculated as % ID/gram of wet tissue and tumor-to-tissue ratios.

Figure 7B:
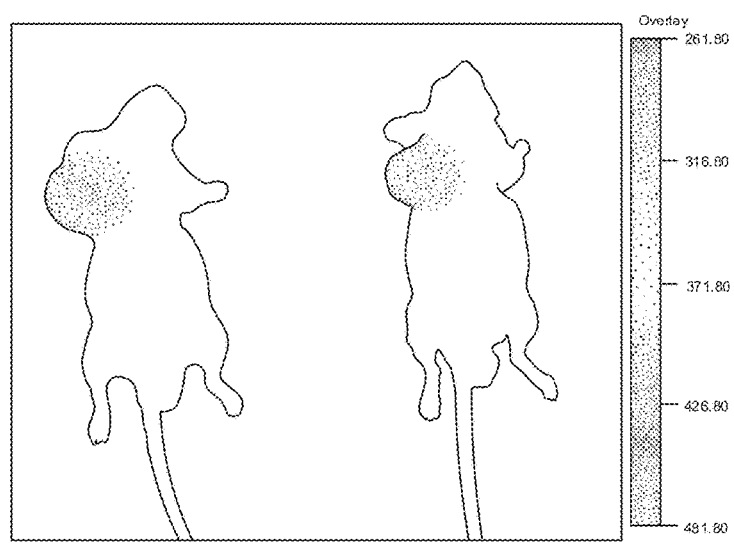
FIG. 7B is a set of whole body mice images showing HEK 293-NK1R tumor xenograft model treated with the NK1RL-EC20 peptide linker-$^{99m}$Tc conjugate (left), and showing blocking (right).

FIG. 7B is a set of whole body mice images of mice for NK1RL-EC20 peptide linker-99mTc conjugate, showing on the left a HEK 293-NK1R tumor xenograft model treated with NK1RL-EC20 peptide linker-$^{99m}$Tc conjugate, and on the right the HEK 293-NK1R tumor xenograft model aged mouse with blocking.

Figure 7C:
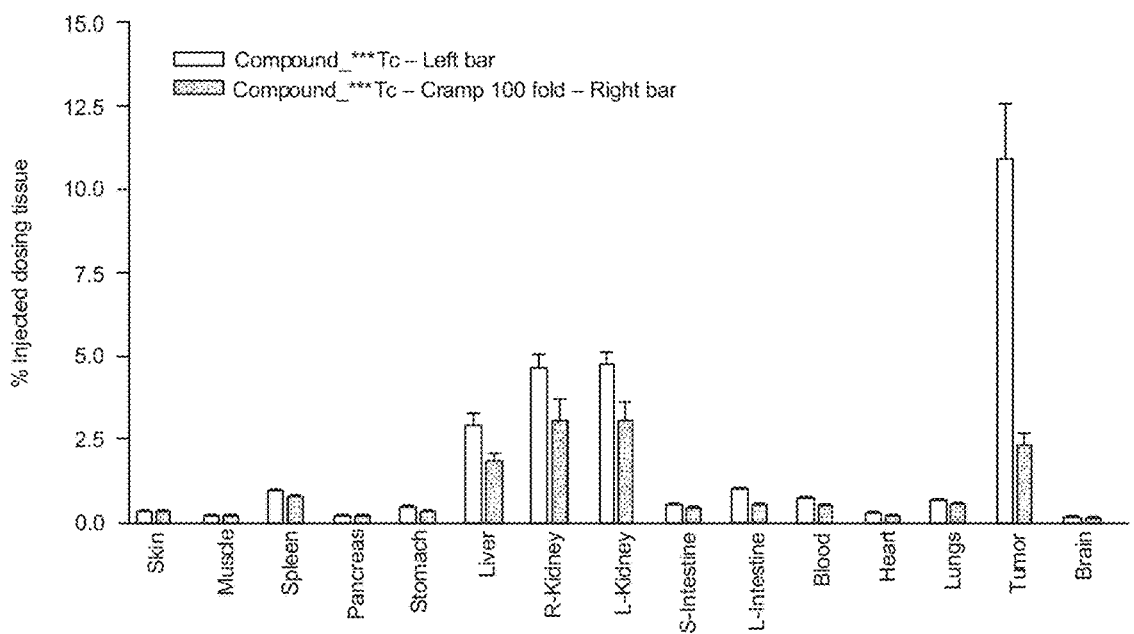
FIG. 7C is a biodistribution study of the imaged mice from FIG. 7B for the NK1RL-EC20 peptide linker-$^{99m}$Tc conjugate and a competitive NK-1 receptor ligand.
Figure 7D:
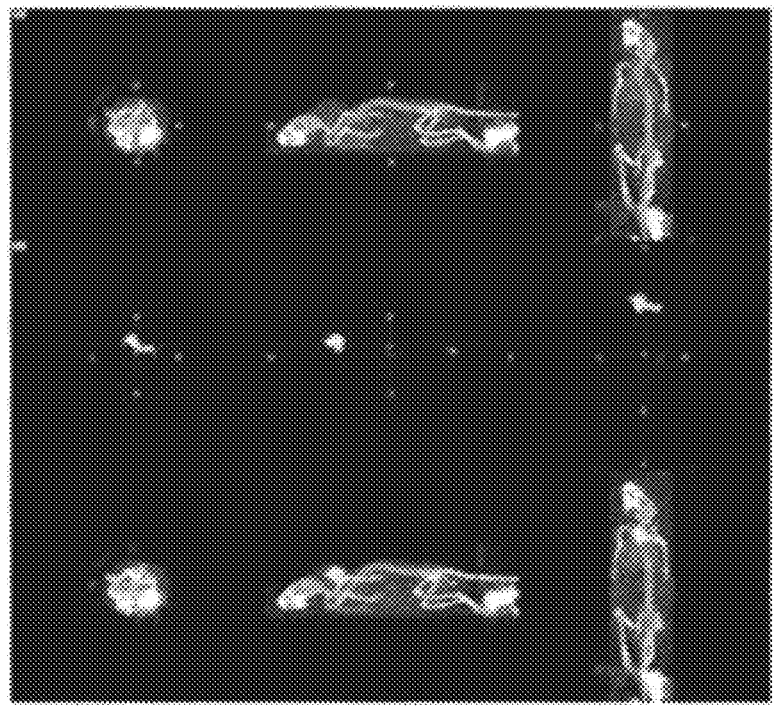
FIG. 7D is a set of whole body mice images on SPECT-CT for NK1RL-EC20 peptide linker-$^{99m}$Tc conjugate in HEK 293-NK1R tumor xenograft model mice.
Figure 7E:
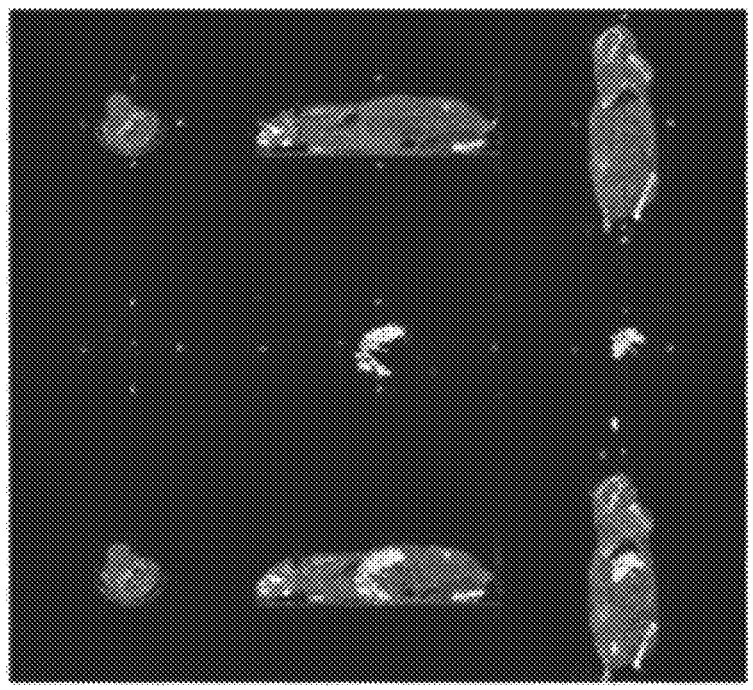
FIG. 7E is a set of whole body mice images on SPECT-CT for NK1RL-EC20 peptide linker-$^{99m}$Tc conjugate in NK1R-negative tumor xenograft model mice.

FIG. 7C shows results from a biodistribution study of mice images for the NK1RL-EC20 peptide linker-$^{99m}$Tc conjugate. For each area, the left-most bar corresponds to administration of NK1RL-EC20 peptide linker-$^{99m}$Tc conjugate, and the right-most bar shows a competitive NK-1 receptor ligand labeled with $^{99m}$Tc. FIG. 7D is a set of whole body mice images on SPECT-CT for NK1RL-EC20 peptide linker-99mTc conjugate in HEK 293-NK1R tumor xenograft model mice. FIG. 7E is a set of whole body mice images on SPECT-CT for NK1RL-EC20 peptide linker-$^{99m}$Tc conjugate in NK1R-negative tumor xenograft model mice.

Example 4

Synthesis of the NK1RL-PEG2-NOTA-Conjugate

NOTA-NHS ester (11 mg, 0.0016 mmol), followed by DIPEA amine in dry DMSO under argon were added to a purified NK1RL-PEG2 linker (10 mg, 0.0016 mmol), created according to procedures described above. The reaction mixture was stirred for 12 hours at room temperature. The reaction progress was confirmed by LC-MS and purified by RP-HPLC (mobile phase A=20 mM ammonium acetate buffer, pH 7, B=acetonitrile, gradient 10-100% B in 30 minutes, 13 mL/min, λ=254 nm). Pure fractions were combined, concentrated under vacuum, and lyophilized to yield the NK1RL-PEG2-NOTA conjugate, which was analyzed by LC-MS and LR-ESIMS.

In Vivo Studies

Figure 8A:
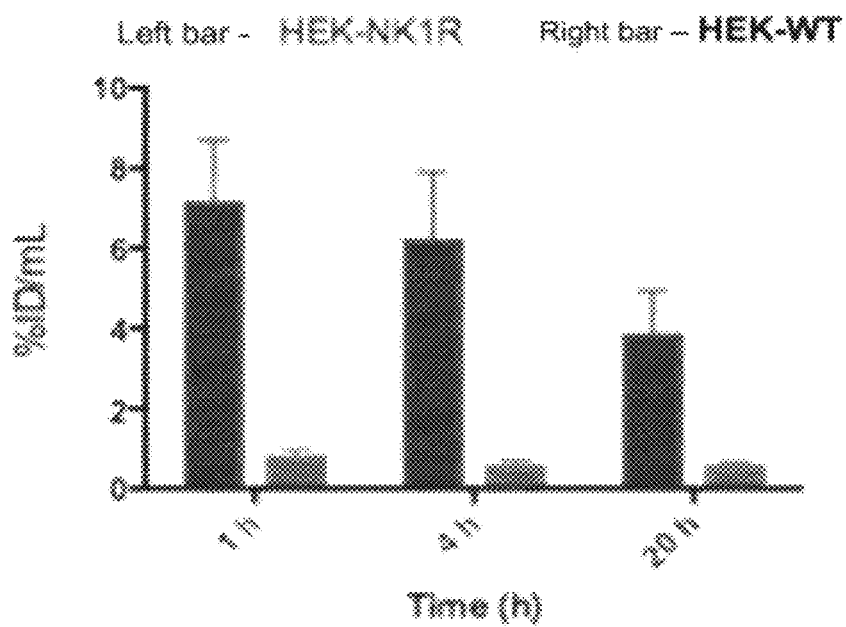
FIG. 8A is a plot showing region of interest (ROI) radioactivity of NK1RL-PEG2-NOTA-$^{64}$Cu conjugate in NK1R-transduced and non-transduced xenografts.
Figure 8B:
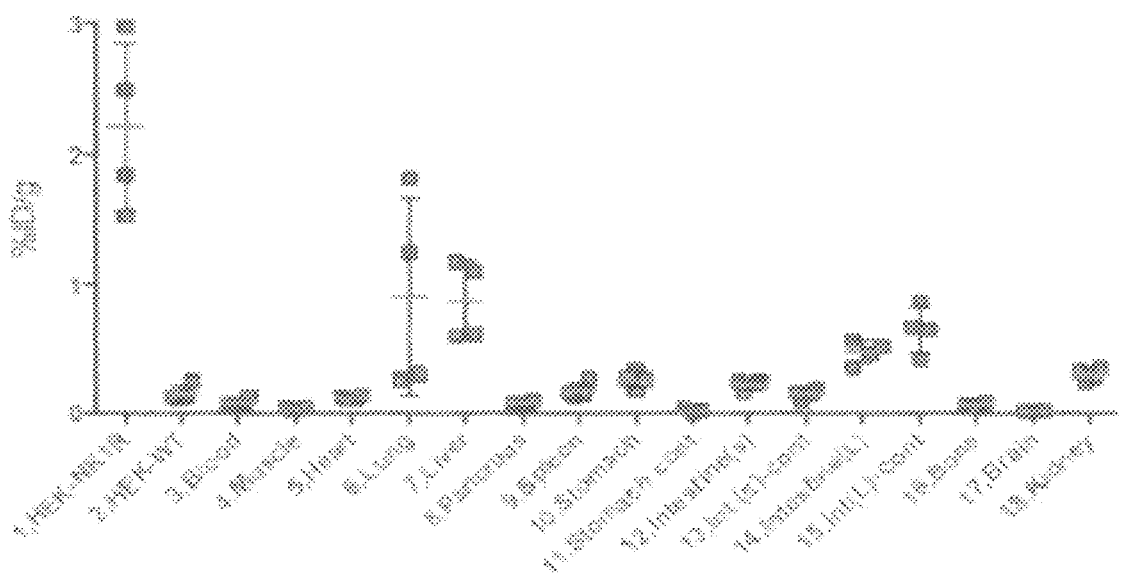
FIG. 8B is a plot showing the NK1RL-PEG2-NOTA-$^{64}$Cu conjugate uptake ratio between the NK1R-transduced and non-transduced xenografts in various areas at 20 hours post-injection.

A NK-1 receptor-binding radionuclide delivery conjugate was prepared that contained NK1RL, a PEG2 linker, and $^{64}$Cu-labeled chelator (radiochemical purity: 99%) with Specific Activity (SA) of 3.7 MBq/μg. Four NKIR-transduced xenografts (HEK 293-NKIR) were prepared, as well as four non-transduced xenografts (HEK 293-WT) using athymic nude mice. Doses of 140-160 uCi (~2 moles) of ligand per mouse were intravenously administered, and the models were imaged at 1, 4 and 20 hours post-injection using PET. The images were analyzed in a region of interest (ROI) around the tumor xenograft activity, and percentage injected dose per mL (% ID/mL) values were calculated from the mean activity in the ROIs. FIG. 8A is a plot showing ROI activity for the NK1R-transduced and non-transduced xenografts. Therefore, the data showed that the NK1RL-PEG2-NOTA-$^{64}$Cu conjugate specifically accumulated in NK1R-transduced xenografts, but not in non-transduced murine model xenografts. FIG. 8B is a plot showing the $^{64}$Cu—NK1R ligand uptake ratio between the NK1R-transduced and non-transduced xenografts in various areas at 20 hours post-injection.

Analysis of these data showed that that the ratio between NK1R-transduced and non-transduced xenografts was highest at 20 hours post-injection, which may indicate that this radioactive imaging conjugate is more suitable for imaging at a relatively late time point after administration.

Figure 8C:
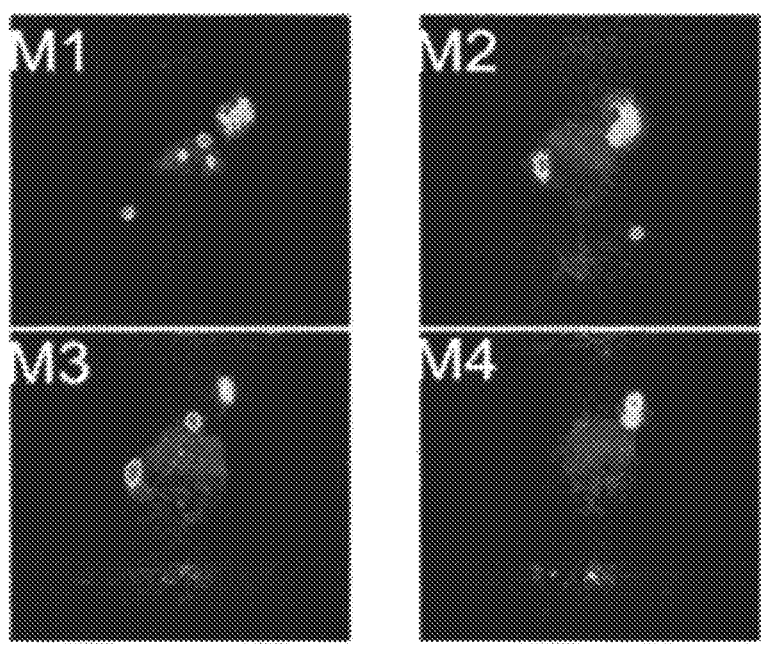
FIG. 8C is a set of PET images showing HEK 293-NK1R tumor xenograft model mice treated with a conjugate in which the active agent has $^{64}$Cu.

FIG. 8C is a set of HEK 293-NK1R tumor xenograft model mice on PET using a conjugate in which the active agent has $^{64}$Cu.

Example 5

Synthesis of the NK1RL-PEG36-Based Short EC20 Linker-$^{99m}$Tc Conjugate

A solution of sodium pertechnetate (1.0 mL, 15 mCi) was added to a vial containing a lyophilized mixture of NK1RL-EC20 peptide linker (0.178 mg), sodium α-D-glucoheptanoate dehydrate (80 mg), stannous chloride dihydrate (0.8 mg), and sufficient NaOH to achieve pH of 7.2 upon rehydration with water. After adding sodium pertechnetate (15 mCi), the vial was heated in a boiling water bath for 18 minutes and then cooled to room temperature before use. The labeling efficiency, radiochemical purity, and radiochemical stability were analyzed by RP-HPLC.

In Vitro Studies

Figure 9A:
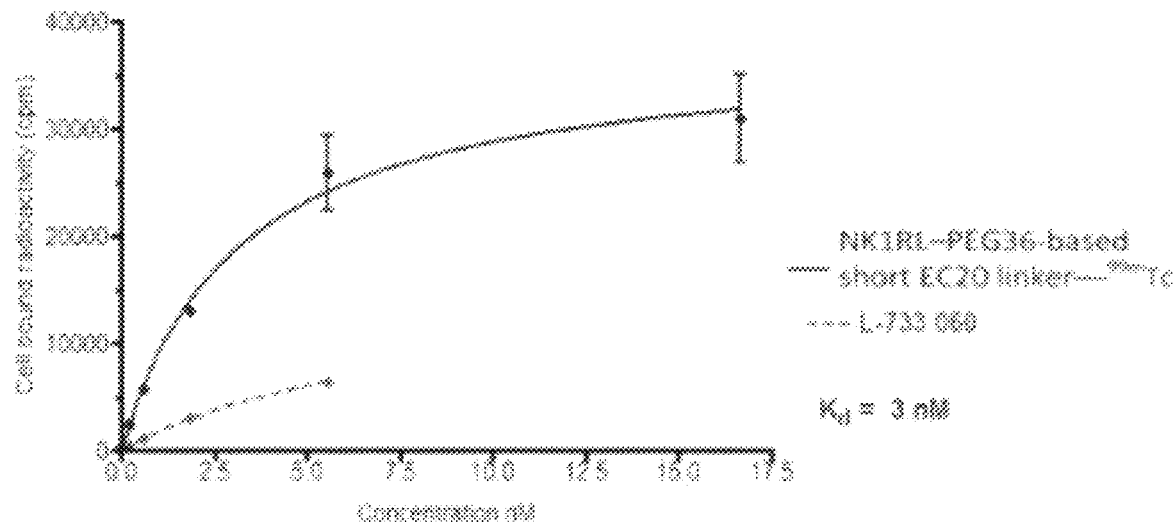
FIG. 9A is a plot showing the radioactivity binding affinity of an NK1RL-PEG36-based short EC20 linker-$^{99m}$Tc conjugate versus concentration of the conjugate in cells in the presence and absence of a competing ligand.
Figure 9A:
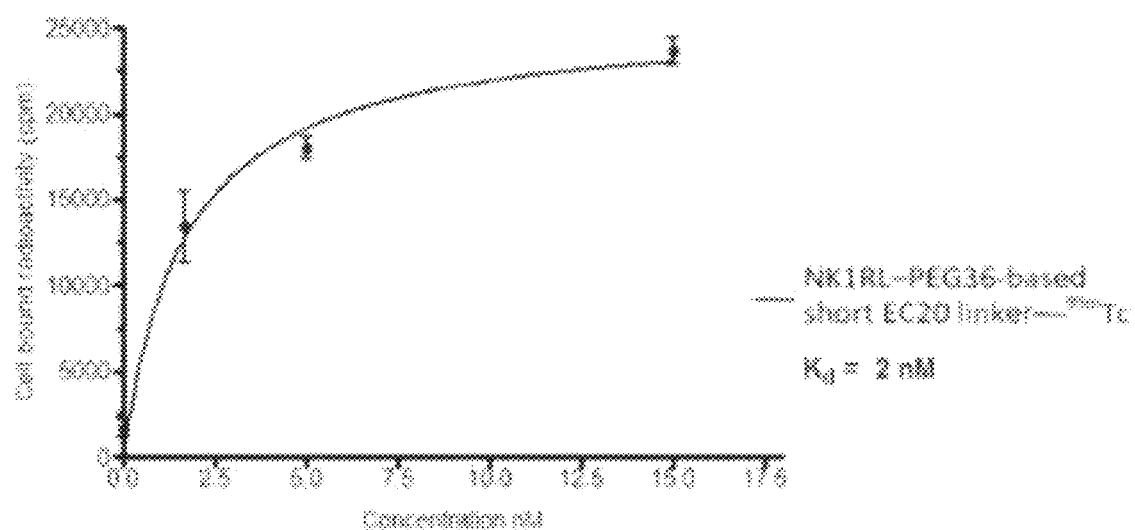

HEK 293 NK1R cells (50,000 cells/well) were seeded into 24 well plates (BD Purecoat Amine, BD Biosciences) and allowed to grow to confluence over 48-72 hours. Spent medium in each well was replaced with 0.5 mL of fresh medium containing 0.5% bovine serum albumin and increasing concentrations of NK1RL-PEG36-containing short EC20 linker-$^{99m}$Tc in the presence or absence of 100-fold excess of competing ligand, i.e., L-733,060. After incubation for 1 hour at 37° C., cells were rinsed with incubation solution (3×0.5 mL) to remove unbound radioactive material and cells were dissolved in 0.25 M NaOH aqueous (0.5 mL) solution. The dissolved cells were transferred into individual γ-counter tubes and radioactivity was counted using a γ-counter. The binding constant (Kd) was calculated by plotting bound radioactivity versus the concentration of targeted radiotracer using GraphPad Prism 4 program. FIG. 9A illustrates this binding data for NK1RL-PEG36-containing short EC20 linker-$^{99m}$Tc in the presence of the competing ligand (top) and without the competing ligand (bottom).

In Vivo Studies

Four- to six-week old male nu/nu mice were inoculated subcutaneously on their shoulders with HEK 293 NK1R cells (5.0×106 cells/mouse in 50% HC Matrigel) using a 25-gauge needle. Growth of the tumors was measured in two perpendicular directions every 2 days using a caliper, and the volumes of the tumors were calculated as 0.5×L×W2 (L=measurement of longest axis, and W=axis perpendicular to L in millimeters). Animals were treated with NK1RL-PEG36-containing short EC20 linker-$^{99m}$Tc (2 nmol, 150 μCi) in saline (100 μL) when the tumors reached 300-500 mm$^3$ volume (~3 weeks). Experiments on live mice involved three mice per group, animals were sacrificed by CO$_2$ asphyxiation at different time points as described below. Images were acquired by a Kodak Imaging Station in combination with CCD camera and Kodak molecular imaging software (version 4.0) (radioimages: illumination source=radio isotope, acquisition time=2 and 4 min, f-stop=0, focal plane=5, FOV=162.5, binning=4; White light images: illumination source=white light transillumination, acquisition time=0.175 sec, f-stop=11, focal plane=5, FOV=162.5 with no binning).

Following imaging, animals were dissected and selected tissues were collected into pre-weighed γ-counter tubes. Radioactivity of pre-weighed tissues and NK1RL-PEG36-containing short EC20 linker-$^{99m}$Tc (2 nmol, 150 μCi) in saline (100 μL) was counted in a γ-counter. CPM values were decay corrected and results were calculated as % ID/gram of wet tissue and tumor-to-tissue ratios.

Figure 9B:
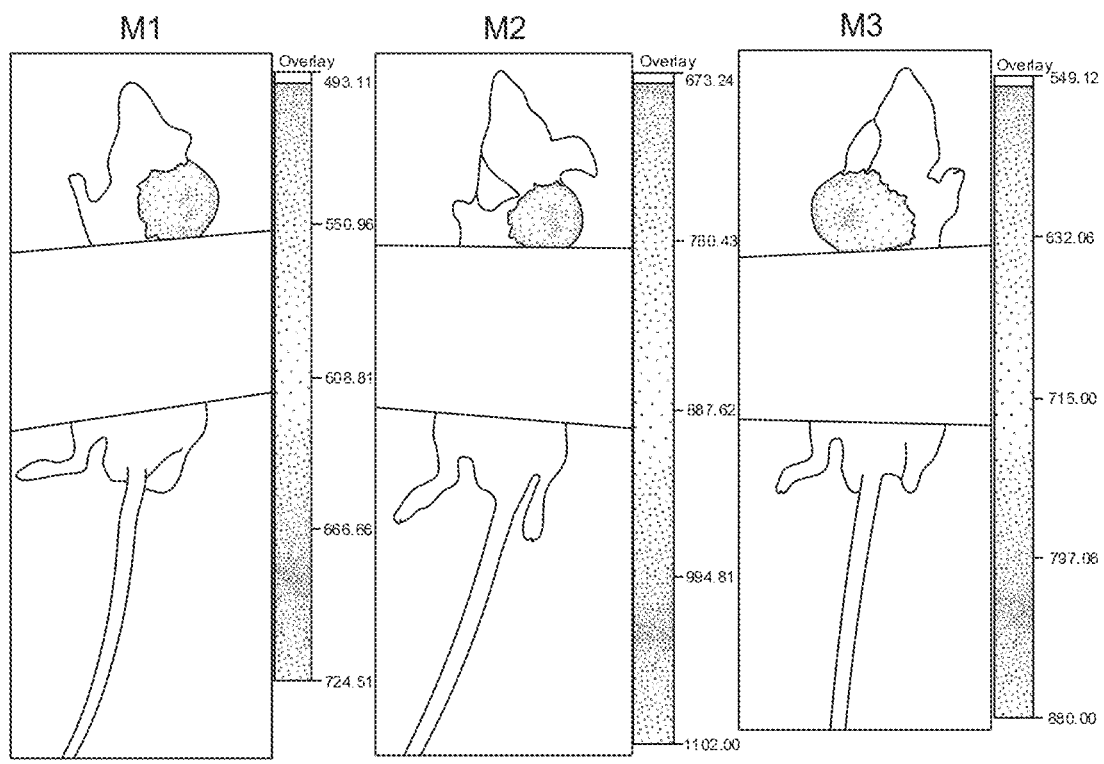
FIG. 9B is a set of whole body mice images showing HEK 293-NK1R tumor xenograft model treated with the NK1RL-PEG36-based short EC20 linker-$^{99m}$Tc conjugate with shielding (top row), and without shielding (bottom row).
Figure 9B:
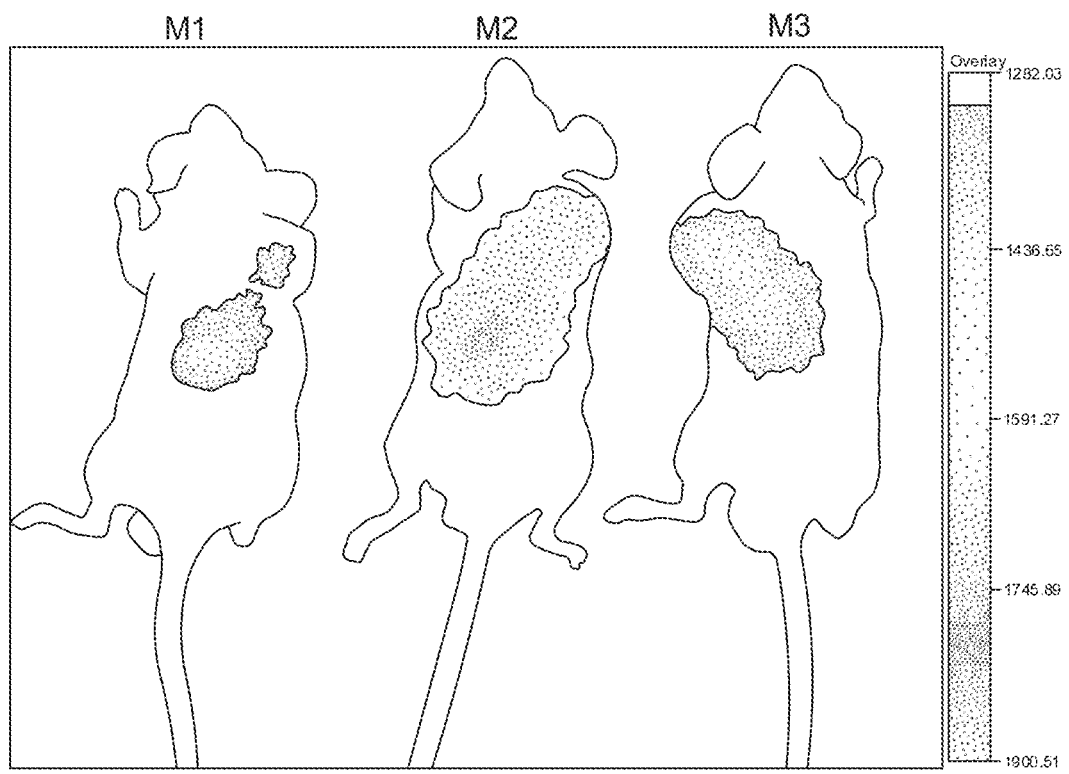

FIG. 9B is a set of whole body mice images of mice for NK1RL-PEG36-containing short EC20 linker-$^{99m}$Tc conjugate, showing in the upper row a HEK 293-NK1R tumor xenograft model group with a lead shield positioned to allow observation of the relative radioactivity in only the tumor areas. The lower row shows a HEK 293-NK1R tumor xenograft model group treated with NK1RL-PEG36-containing short EC20 linker-$^{99m}$Tc conjugate without shielding.

Figure 9C:
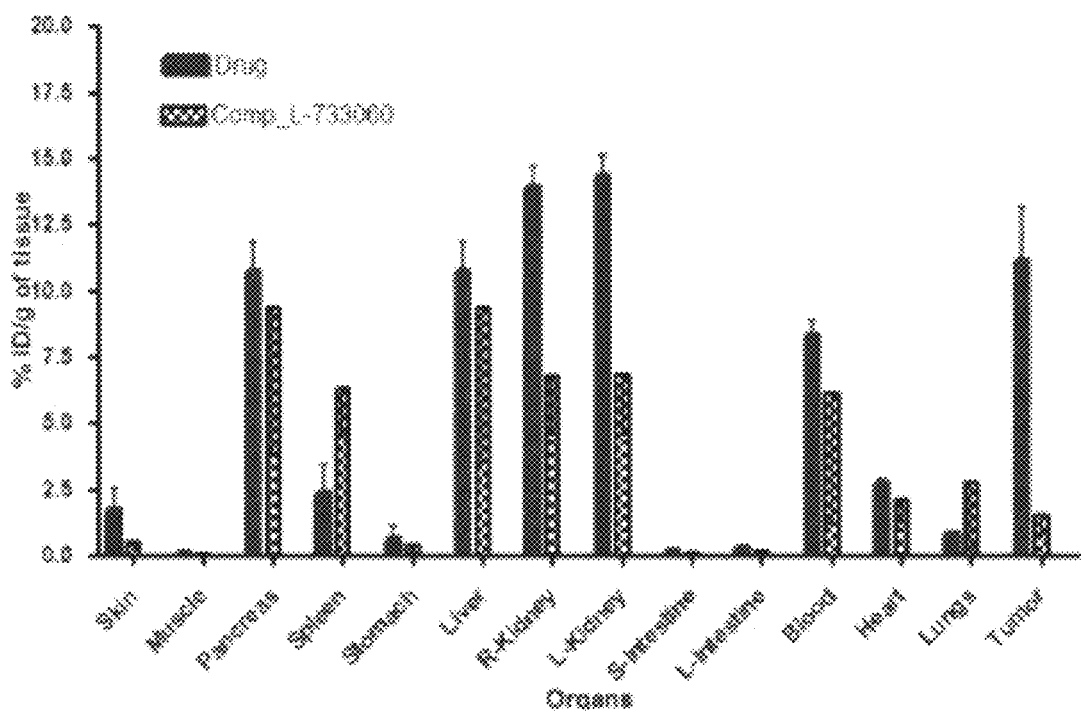
FIG. 9C is a biodistribution study of the imaged mice from FIG. 9B for the NK1RL-PEG36-based short EC20 linker$^{99m}$Tc conjugate and a competitive NK-1 receptor ligand at 2 hours post-injection.
Figure 9D:
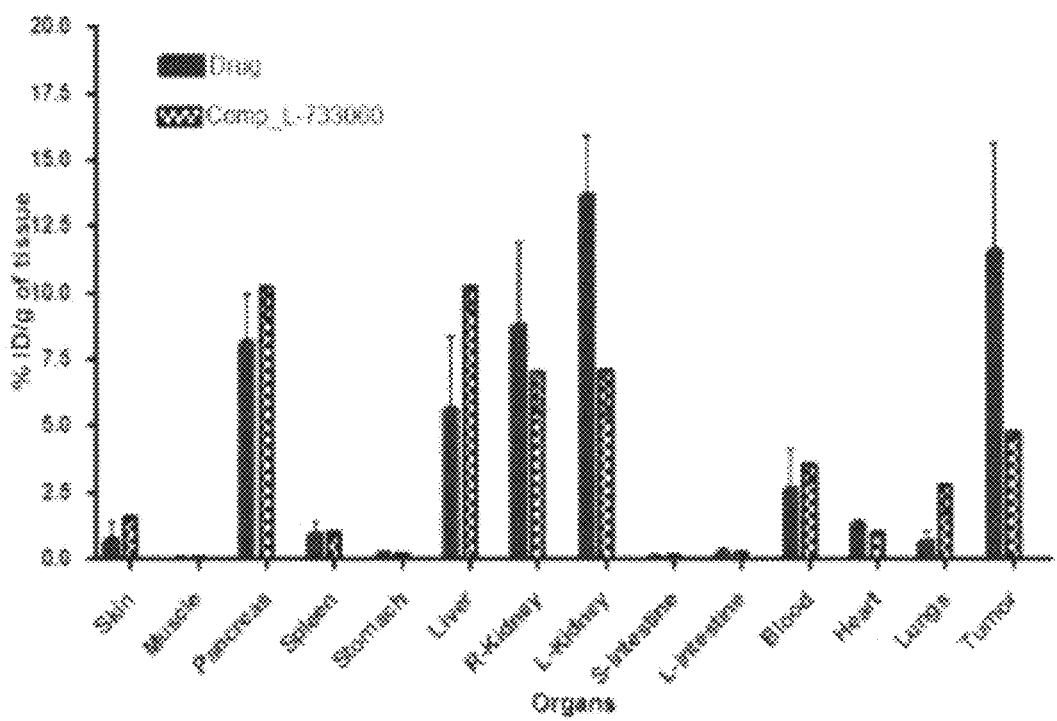
FIG. 9D is a biodistribution study of the imaged mice from FIG. 9B for the NK1RL-PEG36-based short EC20 linker-$^{99m}$Tc conjugate and a competitive NK-1 receptor ligand at 8 hours post-injection.

FIGS. 9C and 9D show results from a biodistribution study of mice images for the NK1RL-PEG36-containing short EC20 linker-$^{99m}$Tc at 2 hours and 8 hours post-injection, respectively. For each area, the left-most bar corresponds to administration of NK1RL-PEG36-containing short EC20 linker-$^{99m}$Tc conjugate, and the right-most bar shows a competitive NK-1 receptor-binding ligand (L-733,060) labeled with $^{99m}$Tc.

Example 6

Figure 10A:
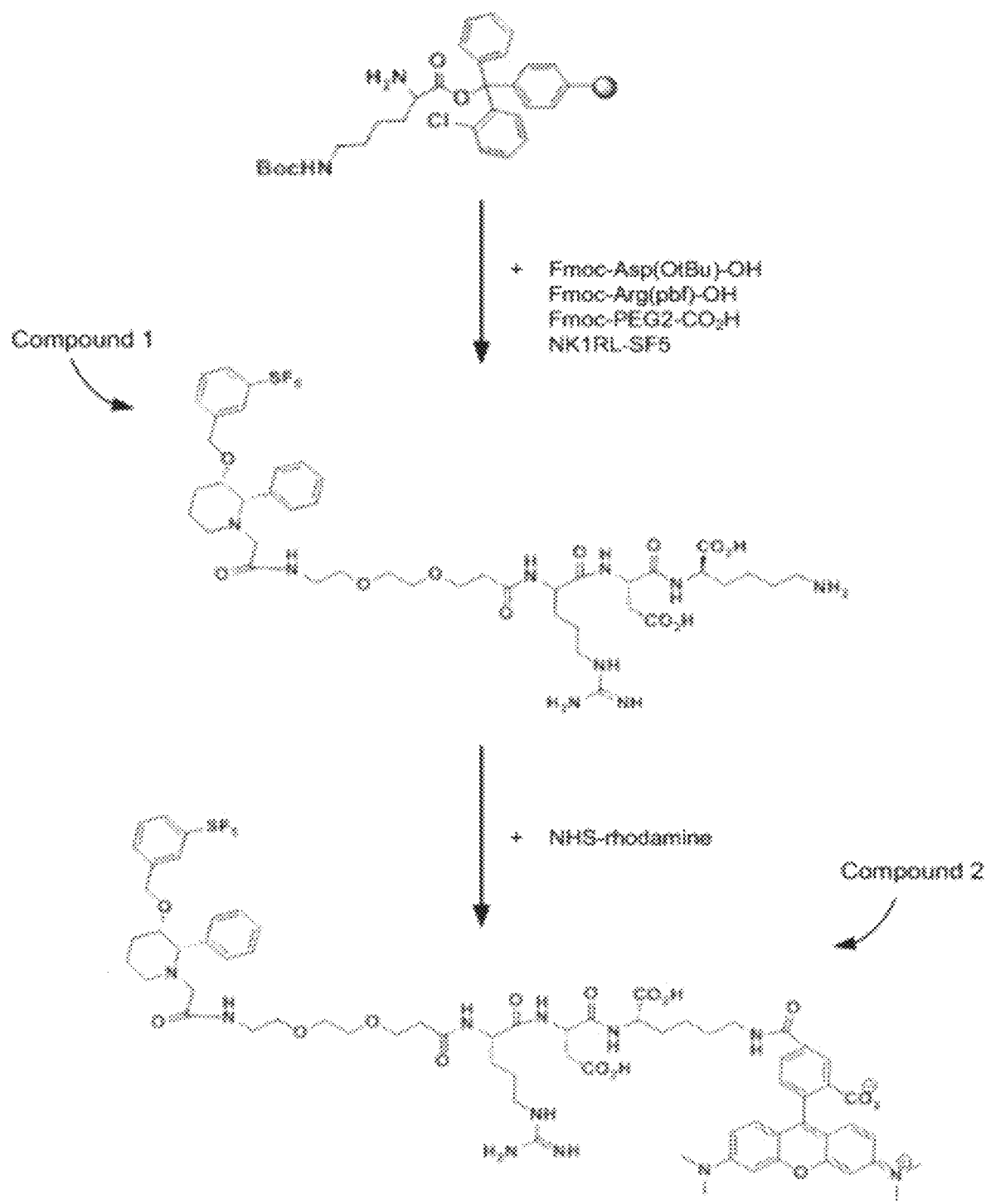
FIG. 10A is a schematic reaction equation illustrating the synthesis of an NK1RL-SF5-Lys peptide linker-rhodamine conjugate.

As illustrated in FIG. 10A, synthesis of NK1RL-SF5-Lys peptide linker-rhodamine conjugate was carried out by synthesizing the NK1RL-SF5 NK-1 receptor-binding moiety, which was used to create the NK1RL-SF5-Lys peptide linker, to which NHS-rhodamine was added. Specifically, NK1RL-SF5-Lys peptide linker-rhodamine conjugate synthesis was performed using the following steps.

Synthesis of NK1RL-SF5

Synthesis of an alternative NK-1 receptor-binding moiety NK1RL-SF5, discussed above, was carried out using the following steps.

Starting with (2S,3S)-3-(3-pentatrifluoromethyl)benzyloxy)-2-phenylpiperidine (1, 0.055 g, 0.00013 mmol) in dry THF (1.0 mL), were added tri ethylamine (TEA) (0.048 mL, 0.00034 mmol, 2.5 equiv), followed by tert-butyl-2-bromo acetate (0.03 mL, 0.00021 mmol, 1.5 equiv) under N$_2$. The reaction was stirred for 16 hours at room temperature, The reaction was quenched with water and 2% HCl solution, and extracted with ethyl acetate (EtOAc) (3×5 mL). The combined organic layers were washed with brine, dried with sodium sulfate (Na$_2$SO$_4$), filtered, and concentrated. The resulting residue was purified using silica-gel column chromatography (hexance:EtOAc, 4:1) to give an intermediary ester (0.070 g, 93%) according to the formula:

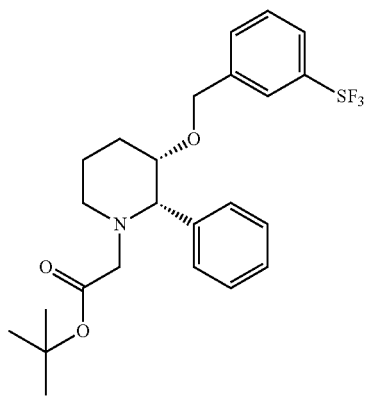

TFA (20 equiv) was added to the intermediary ester (0.07 g, 0.00013 mmol) in dry CH$_2$Cl$_2$, and stirred for 4 hours at room temperature. The excess of TFA was removed and diluted with water, extracted with CH$_2$Cl$_2$ (3×5 mL). The combined organic layers were washed with brine, dried (Na$_2$SO$_4$) and concentrated. The residue obtained was purified by flash silica-gel column chromatography (hexane:EtOAc, 3:7) to give a product NK1RL-SF5 (0.052 g, 90%).

Synthesis of NK1RL-SF5-Lys Peptide Linker

An NK1RL-SF5-Lys peptide linker was synthesized by following an analogous procedure to that used to synthesize the NK1RL-Lys peptide linker as discussed above with respect to FIG. 2. The NK1RL-SF5-Lys peptide linker was then purified through RP-HPLC and characterized accordingly as described above.

Synthesis of NK1RL-SF5-Lys Peptide Linker-Rhodamine Conjugate

The purified NK1RL-SF5-Lys peptide linker (Compound 1 in FIG. 10A) was coupled with NHS-rhodamine by stirring 1:1.2 ratios of the NK1RL-SF5-Lys peptide linker and NHS-rhodamine in dry DMSO, DIPEA under argon for 12 hours at room temperature. The resulting material was purified by RP-HPLC (mobile phase A=20 mM ammonium acetate buffer, pH 7, B=acetonitrile, gradient 10-100% B in 30 min, 13 mL/min, λ=280 nm). Pure fractions were combined, concentrated under vacuum, and lyophilized to yield the product, NK1RL-SF5-Lys Peptide linker-rhodamine conjugate (Compound 2 in FIG. 10A). The NK1RL-SF5-Lys peptide linker-rhodamine conjugate, a reddish solid, was analyzed using LC-MS and LR-ESIMS.

Figure 10B:
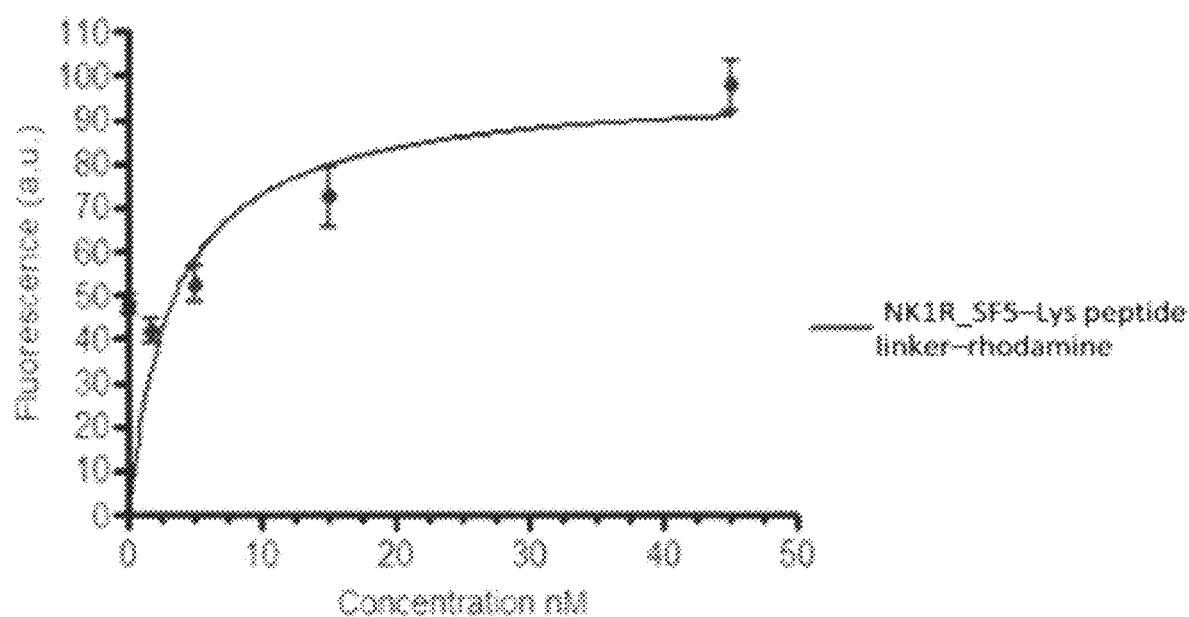
FIG. 10B is a plot showing the fluorescence binding affinity of an NK1RL-SF5-Lys peptide linker-rhodamine conjugate in cultured HEK 293-NK1R cells expressing NK-1 receptor.

FIG. 10B shows the binding affinity of the NK1RL-SF5-Lys peptide linker-rhodamine conjugate in cultured HEK 293-NK1R cells expressing NK-1 receptor.

Fluorescent Confocal Microscopy Imaging

HEK 293-NK1R cells (50,000 cells/well in 0.5 mL) were seeded into confocal microwell plate (Lab-Tek, Chambered #1.0 Borosilicate Coverglass) and allowed cells to form monolayers over 24 hours. Spent medium was replaced with fresh medium containing NK1RL-SF5-Lys peptide linker-rhodamine (25 nM) in the presence or absence of 100-fold excess free ligand and cells were incubated for 1 hour at 37° C. After washing with fresh medium (3×0.5 mL), confocal images were acquired using a confocal microscopy (FV 1000, Olympus).

Figure 10C:
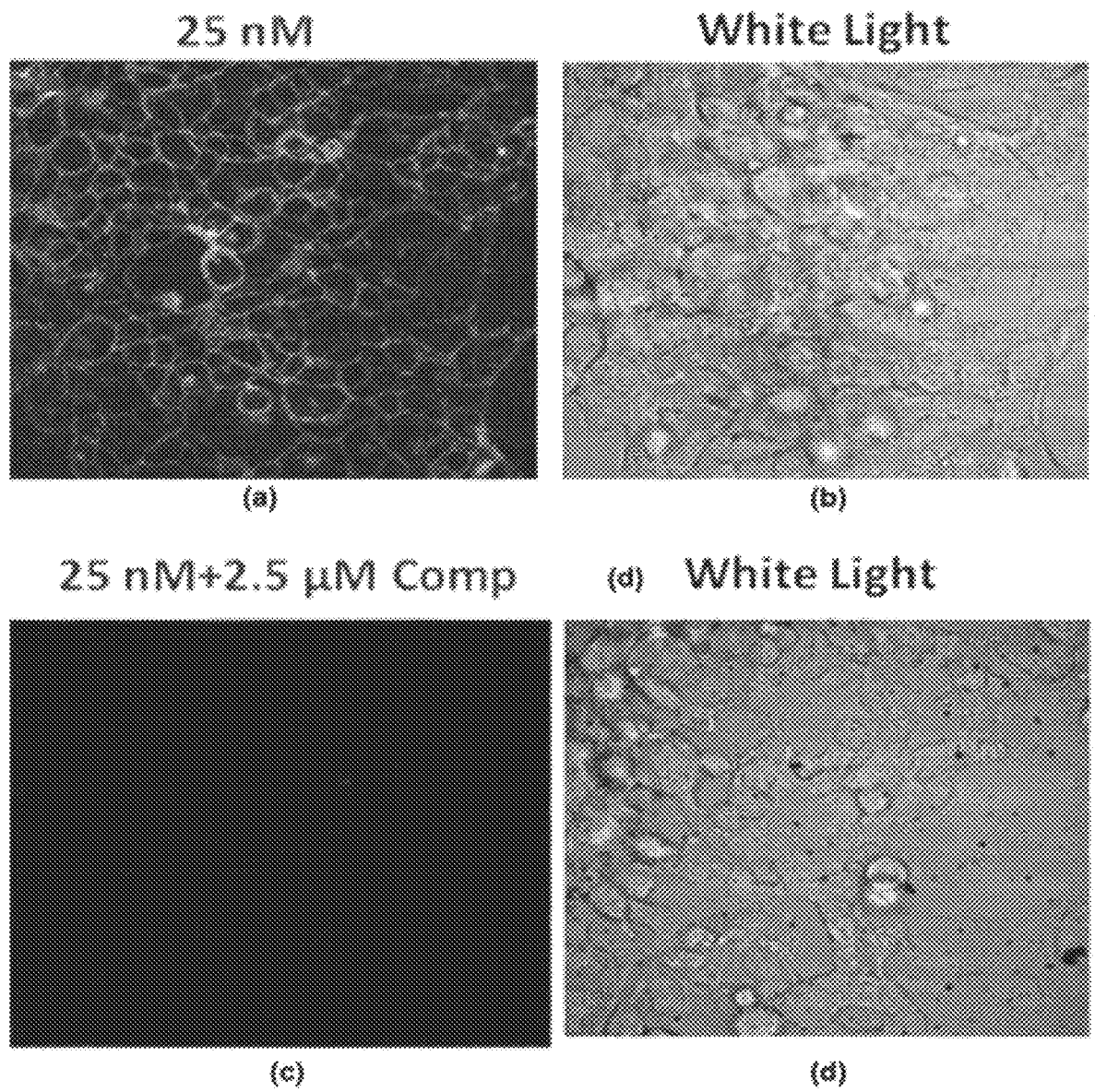
FIG. 10C is a set of confocal microscopy images showing in vitro binding of NK1RL-SF5-Lys peptide linker-rhodamine to HEK 293-NK1R cells.

FIG. 10C shows resulting images from the binding studies of the NK1RL-SF5-Lys peptide linker-rhodamine conjugate to HEK 293-NK1R cells. Specifically, the confocal images provide (a) a magnification of cells after incubation for 1 hour at 37° C. in the absence of competing agent, (b) a magnified white light image of the cells in (a), (c) a magnification of the cells in the presence of a 100-fold excess of competing agent (NK1RL alone) to the conjugate at 25 nM concentration, and (d) a magnified white light image of the cells in (c).

Example 7

Synthesis of NK1RL-SF5-Tyrosine peptide linker-S0456

Figure 11:
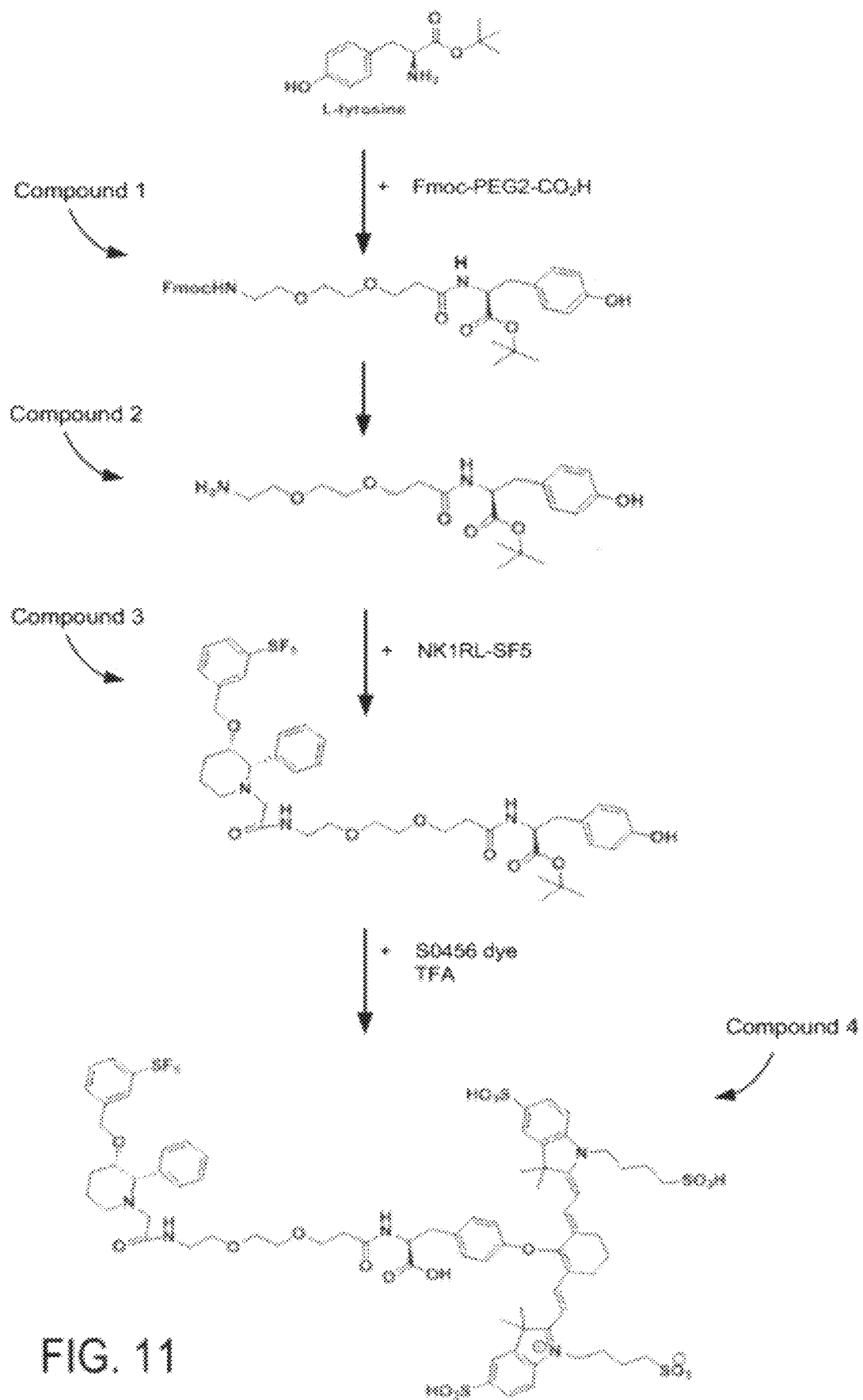
FIG. 11 is a schematic reaction equation illustrating the synthesis of an NK1RL-SF5-tyrosine peptide linker-S0456 conjugate.

A fluorescent imaging conjugate, NK1RL-SF5-tyrosine peptide linker-S0456, was synthesized, as illustrated in FIG. 11, according to the following steps.

Starting with a mixture of tert-butyl-L-tyrosine (1.1 equiv) and Fmoc-PEG2-CO$_2$H in CH$_2$Cl$_2$, 1-[Bis(dimethylamino)methylene]-1H-1,2,3-triazolo[4,5-b]pyridinium 3-oxide hexafluorophosphate (HATU) (1.2 equiv) was added, followed by DIPEA (5.0 equiv) under nitrogen. The reaction mixture was stirred for 12 hours at room temperature. The reaction was then quenched with water and 2% HCl solution, and extracted with EtOAc (3×5 mL). The combined organic layers were washed with brine, dried using sodium sulfate, filtered, and concentrated. The resulting residue was purified by silica-gel column chromatography (hexane:EtOAc, 4:1) to afford a first intermediary (Compound 1 in FIG. 11), which was confirmed by LC-MS.

Piperidine in THF (1:1) was added to the pure Compound 1 under nitrogen and stirred for 2 hours at room temperature. Completion of the reaction was confirmed by LC-MS, and an excess of solvent and piperidine were evaporated, resulting in a second intermediary (Compound 2 in FIG. 11).

Compound 2 (1.0 equiv) was mixed with NK1RL-SF5 (1.0 equiv) in CH$_2$Cl$_2$. HATU (1.2 equiv) was added to the mixture, followed by DIPEA (5.0 equiv) under nitrogen. The reaction mixture was stirred for 12 hours at room temperature. The reaction was quenched with water and 2% HCl solution, and extracted with EtOAc (3×5 mL). The combined organic layers were washed with brine, dried with sodium sulfate, filtered, and concentrated. The residue was purified by silica-gel column chromatography (hexane:EtOAc, 4:1) to afford a third intermediary (Compound 3 in FIG. 11), which was confirmed by LC-MS.

S0456 dye (1.0 equiv) was added to the pure Compound 3 in DMF, followed by the addition of K$_2$CO$_3$ (5.0 equiv). The reaction mixture was stirred at 60° C. for 4 hours, and at room temperature for 12 hours under nitrogen. The progress of the reaction was monitored and confirmed by LC-MS. After completion of the reaction, crude mass was filtered to remove all solids, and filtrate was stirred with TFA for 1 hour at room temperature. The tert-butyl ester hydrolysis product was confirmed by LCMSand the crude mass was purified by RP-HPLC (mobile phase A=20 mM ammonium acetate buffer, pH 7, B=acetonitrile, gradient 0-80% B in 30 min, 13 mL/min, λ=280 nm). Pure fractions were combined, concentrated under vacuum, and lyophilized to yield the product, NK1RL-SF5-tyrosine peptide linker-S0456 (Compound 4 in FIG. 11). The product Compound 4 was analyzed by LC-MS and LR-ESIMS.

In Vitro Studies

Figure 12:
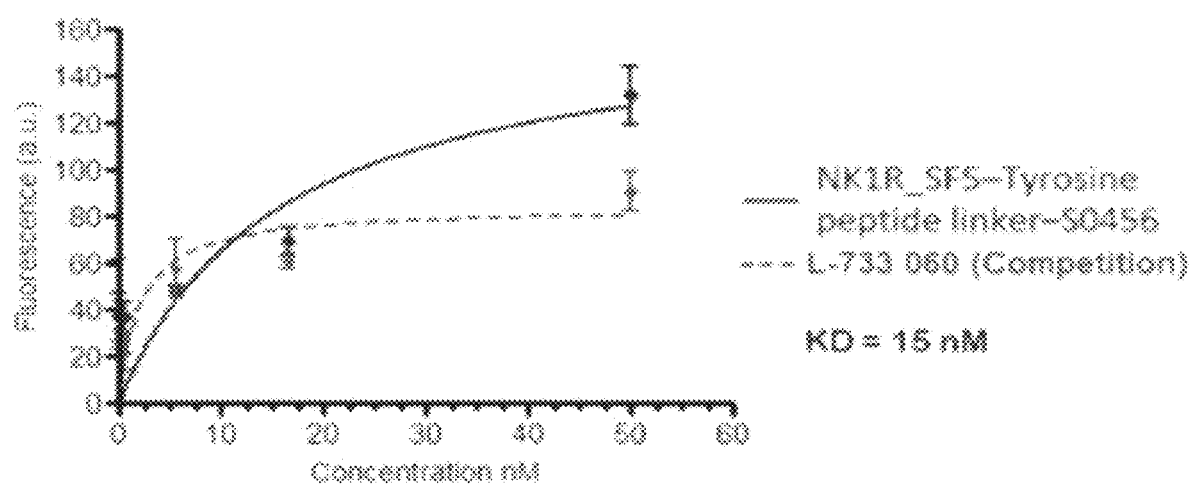
FIG. 12 is a plot showing the fluorescence binding affinity of an NK1RL-SF5-tyrosine peptide linker-S0456 conjugate versus concentration of the conjugate in cells in the presence of a competing ligand.

HEK 293 NKIR cells (50,000 cells/well) were seeded into 24 well plates (BD Purecoat Amine, BD Biosciences) and allowed to grow to confluence over 48-72 hours. Spent medium in each well was replaced with 0.5 mL of fresh medium containing 0.5% bovine serum albumin and increasing concentrations of NK1RL-SF5-Tyrosine peptide linker-S0456 in the presence of 100-fold excess of competing ligand, i.e., L-733,060. The binding constant (Kd) was calculated by plotting fluorescence versus the concentration of targeted radiotracer using GraphPad Prism 4 program, illustrated in FIG. 12.

Example 8

Synthesis of NK1RL-PEG2-DOTA Conjugate

DOTA-NHS ester (6.8 mg, 0.0135 mmol) was added to a purified NK1RL-PEG2 linker (8 mg, 0.0135 mmol), followed by the addition of DIPEA in dry DMSO under argon. The reaction mixture was stirred for 12 hours at room temperature. The reaction progress was confirmed by LC-MS and purified by RP-HPLC (mobile phase A=20 mM ammonium acetate buffer, pH 7, B=acetonitrile, gradient 10-100% B in 30 min, 13 mL/min, λ=254 nm). Pure fractions were combined, concentrated under vacuum, and lyophilized to yield the product, NK1RL-PEG2-DOTA, was analyzed by LC-MS and LR-ESIMS.

In Vivo Studies

Figure 13A:
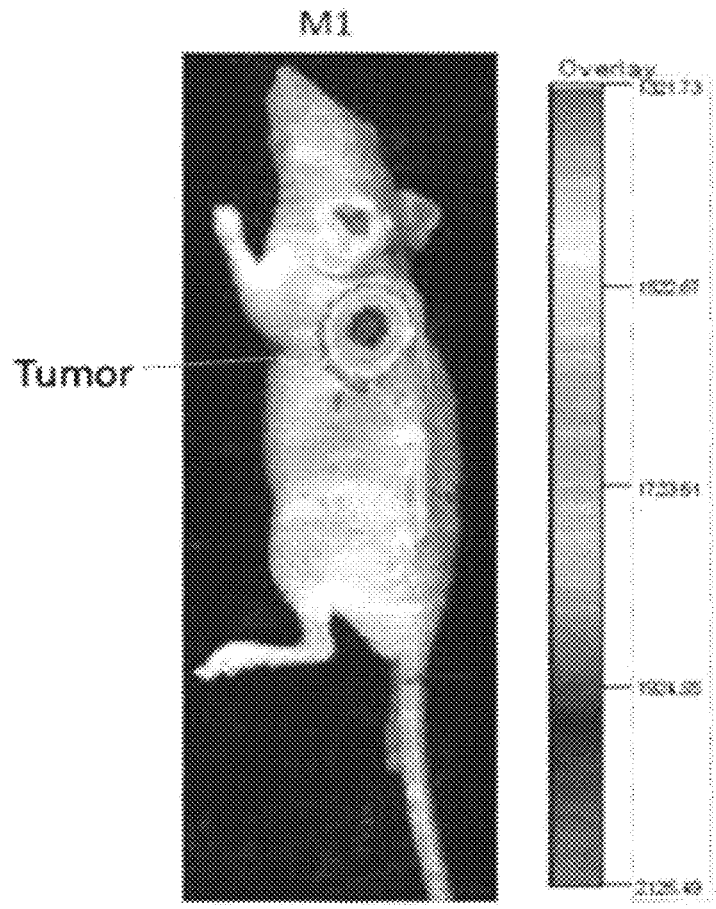
FIG. 13A is a PET image showing a HEK 293-NK1R tumor xenograft model mouse treated with an NK1RL-PEG2-DOTA-$^{111}$In conjugate.
Figure 13B:
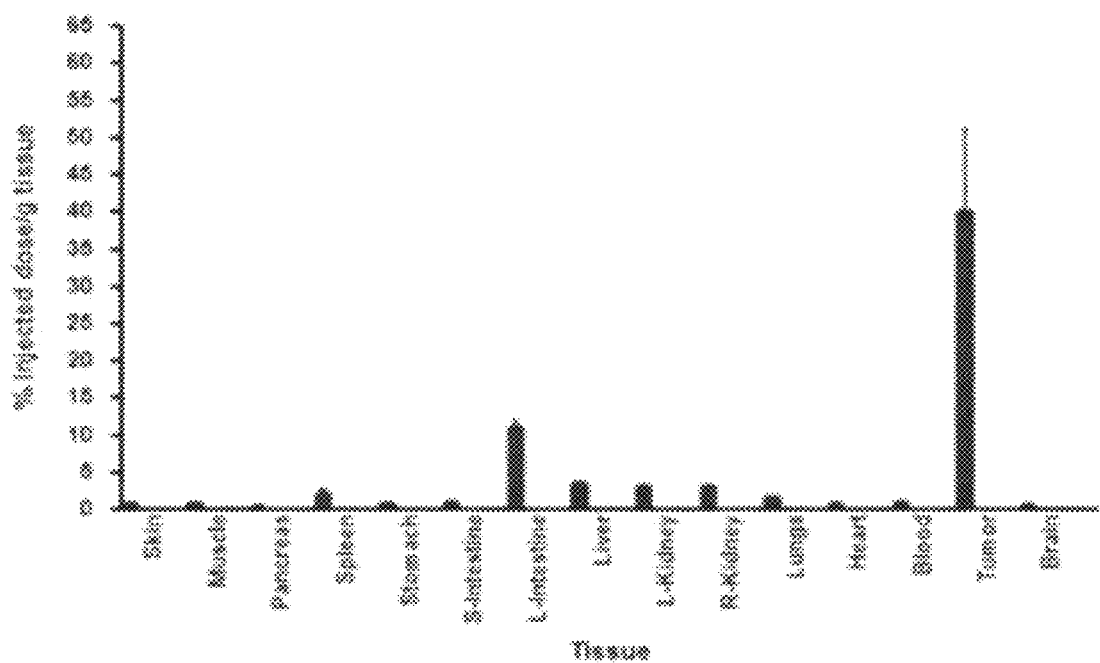
FIG. 13B is a plot showing the NK1RL-PEG2-DOTA-$^{111}$In conjugate uptake ratio in the HEK 293-NK1R tumor xenograft model in various areas at 4 hours post-injection.
Figure 13C:
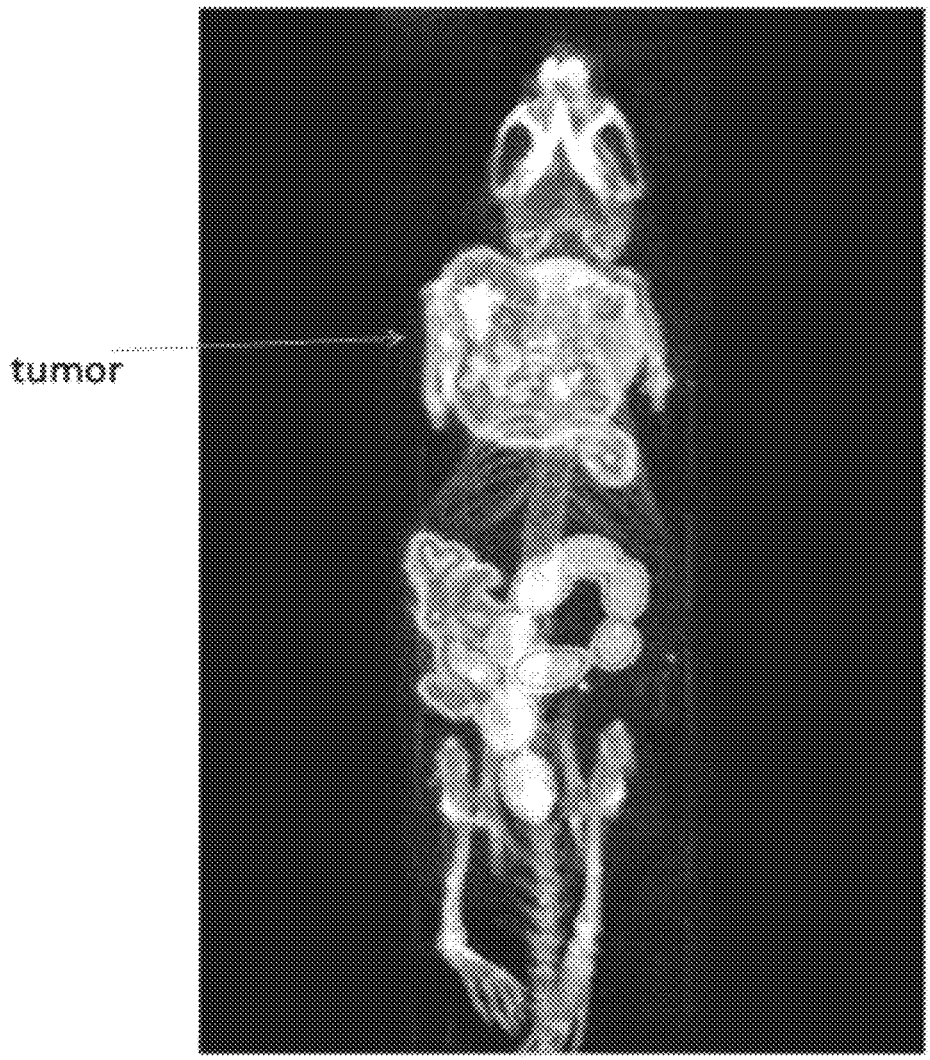
FIG. 13C is a whole body mouse image on SPECT-CT for NK1RL-PEG2-DOTA-$^{111}$In conjugate in the HEK 293-NK1R tumor xenograft mouse.

NK1R-transduced xenografts (HEK 293-NK1R) were prepared in groups, with three mice per group. Doses of around 238 uCi of ligand per mouse were intravenously administered, and the models were imaged at 4 hours post-injection using PET, an example of which is shown in FIG. 13A. The images were analyzed in a region of interest (ROI) around the tumor xenograft activity, and percentage injected dose per mL (% ID/mL) values were calculated from the mean activity in the ROIs. FIG. 13B is a plot showing this ROI activity for the NK1R-transduced xenografts. FIG. 13C is a whole body mouse image on SPECT-CT for the NK1RL-PEG2-DOTA-111In conjugate in a HEK 293-NK1R tumor xenograft model mouse.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

Skilled artisans may implement the above-described methods, processes and/or functionality in varying ways for each particular application, but such implementation decisions should not be interpreted as causing a departure from the scope of the present invention.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A neurokinin-1 (NK-1) receptor-binding agent delivery conjugate, comprising:
   an NK-1 receptor-binding moiety;
   a linker group selected from the group consisting of:

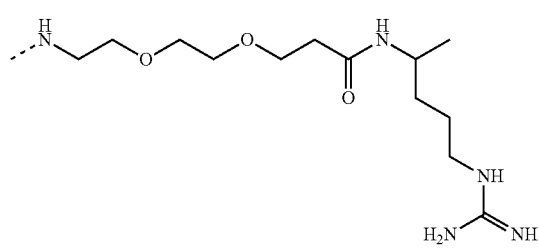

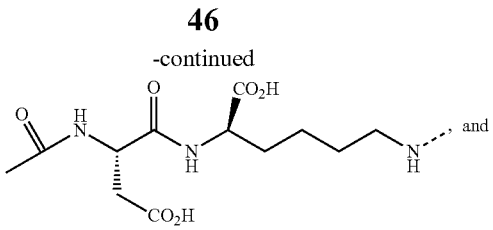

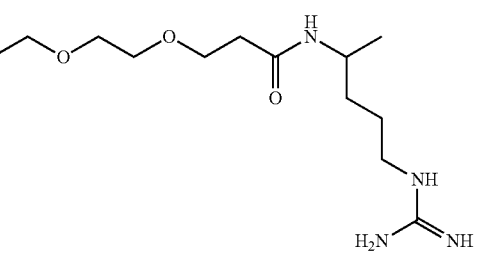

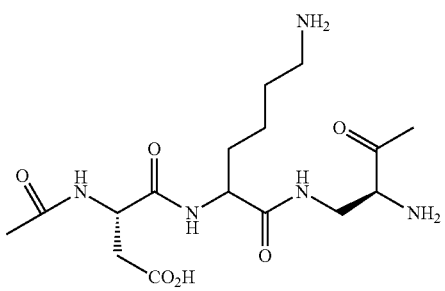

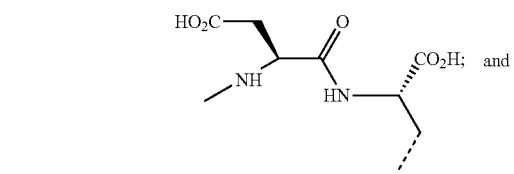

an active agent comprising fluorescein, wherein the NK-1 receptor-binding moiety and the active agent are each bound to the linker group.

2. The NK-1 receptor-binding agent delivery conjugate of claim 1, wherein the active agent further comprises a fluorophore selected from the group consisting of:

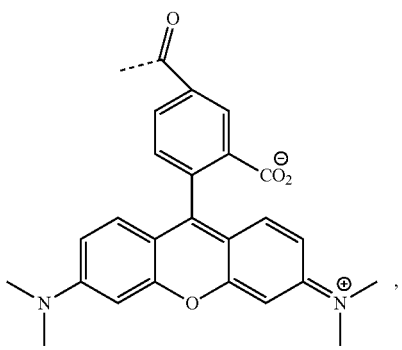

-continued

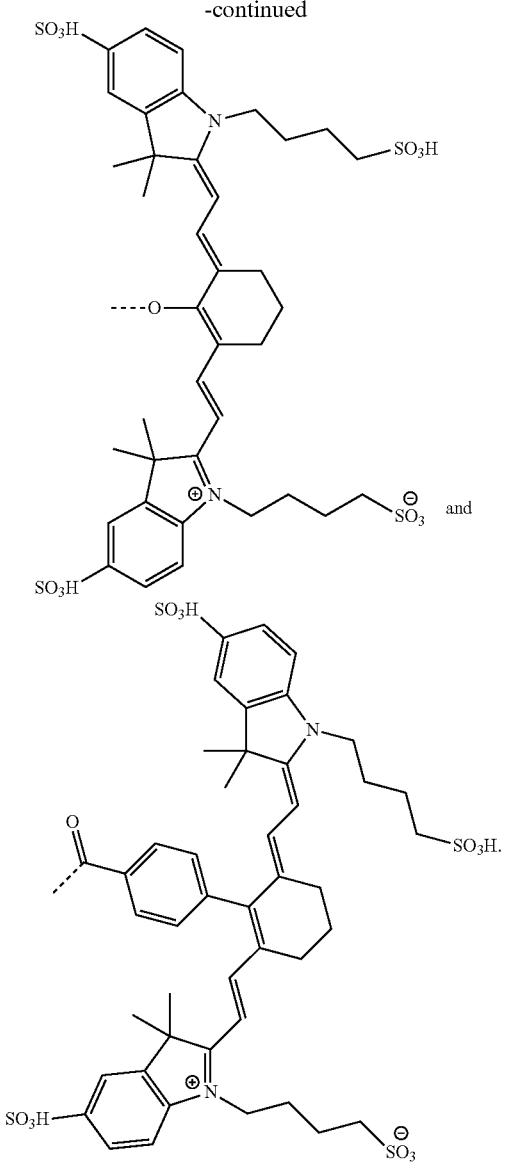

and

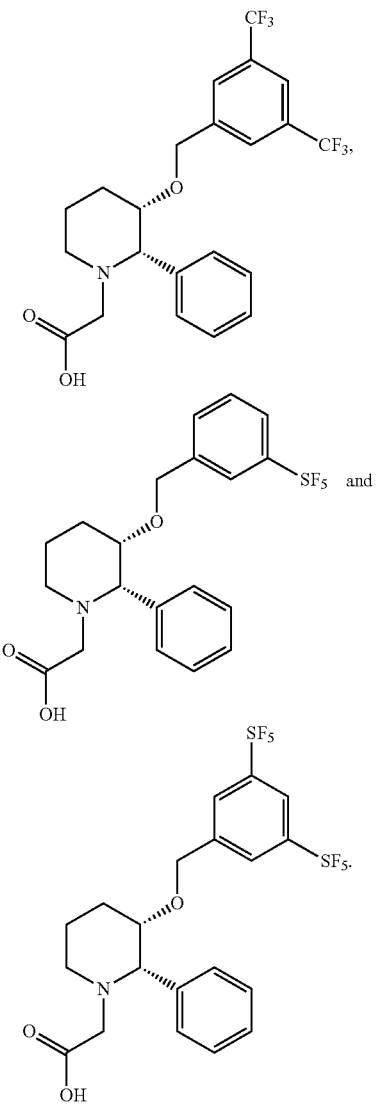

3. The NK-1 receptor-binding agent delivery conjugate of claim 1, wherein the NK-1 receptor-binding moiety comprises a selective NK-1 receptor antagonist or derivative thereof.

4. The NK-1 receptor-binding agent delivery conjugate of claim 1, wherein the NK-1 receptor-binding moiety is selected from the group consisting of:

5. A pharmaceutical composition comprising a NK-1 receptor-binding agent delivery conjugate of claim 1, and a pharmaceutically acceptable carrier, diluent, or excipient therefor.

* * * * *

UNITED STATES PATENT AND TRADEMARK OFFICE
CERTIFICATE OF CORRECTION

PATENT NO. : 11,141,494 B2  
APPLICATION NO. : 15/501630  
DATED : October 12, 2021  
INVENTOR(S) : Kanduluru et al.

Page 1 of 1

It is certified that error appears in the above-identified patent and that said Letters Patent is hereby corrected as shown below:

On the Title Page

Item (54), in "Title", in Column 1, Line 1, before "DEVELOPMENT", insert --DESIGN AND--

Item (87), in "PCT Pub. No.", in Column 1, Line 1, delete "WO2013/126797" and insert --WO2016/025322-- therefor Item (87), in "PCT Pub. Date", in Column 1, Line 1, delete "Aug. 29, 2013" and insert --Feb. 18, 2016-- therefor In the Specification In Column 1, Line 1, before "DEVELOPMENT", insert --DESIGN AND--

Signed and Sealed this  
Thirtieth Day of November, 2021

Drew Hirshfeld  
*Performing the Functions and Duties of the*  
*Under Secretary of Commerce for Intellectual Property and*  
*Director of the United States Patent and Trademark Office*